United States Patent [19]

Ragauskas et al.

[11] Patent Number: 5,388,583
[45] Date of Patent: Feb. 14, 1995

[54] METHOD AND APPARATUS FOR NON-INVASIVELY DERIVING AND INDICATING OF DYNAMIC CHARACTERISTICS OF THE HUMAN AND ANIMAL INTRACRANIAL MEDIA

[75] Inventors: Arminas Ragauskas; Gediminas Daubaris, both of Kaunas, Lithuania

[73] Assignee: UAB Vittamed, Kaunas, Lithuania

[21] Appl. No.: 115,439

[22] Filed: Sep. 1, 1993

[51] Int. Cl.⁶ ............................................... A61B 8/00
[52] U.S. Cl. ......................... 128/661.05; 128/660.02
[58] Field of Search ....................... 128/660.02, 660.05, 128/660.07, 660.09, 661.05, 748

[56] References Cited

U.S. PATENT DOCUMENTS 3,853,117  12/1974  Murr ................................. 128/660.02
5,199,877   4/1993  Page ................................. 128/660.02

OTHER PUBLICATIONS

Freund et al, "Electronic Sector Scanning in the Diagnosis of Cerebrovascular Disease and Space-Occupying Processes", pp. 1147–1159, Reprinted from Neurology, Minneapolis, Nov. 1973, vol. 23, No. 11.

*Primary Examiner*—George Manuel
*Attorney, Agent, or Firm*—St. Onge Steward Johnston & Reens

[57] ABSTRACT

An ultrasonic non-invasive technique is descried for deriving the time dependencies of characteristics of certain regions in the intracranium medium. Precise measurements of the transit travel times of acoustic pulses are made and processed to extract variable portions indicative of, for example, the pulsatility due to cardiac pulses of a basal artery or a cerebroventricle or the variation in the pressure of brain tissue, as well as changes in the cross-sectional dimension of the basal artery and ventricle. In one technique, the transit time variations attributable to cardiac pulses are extracted by processing higher harmonics in the frequency domain. Frequency and phase detection techniques are described.

30 Claims, 16 Drawing Sheets

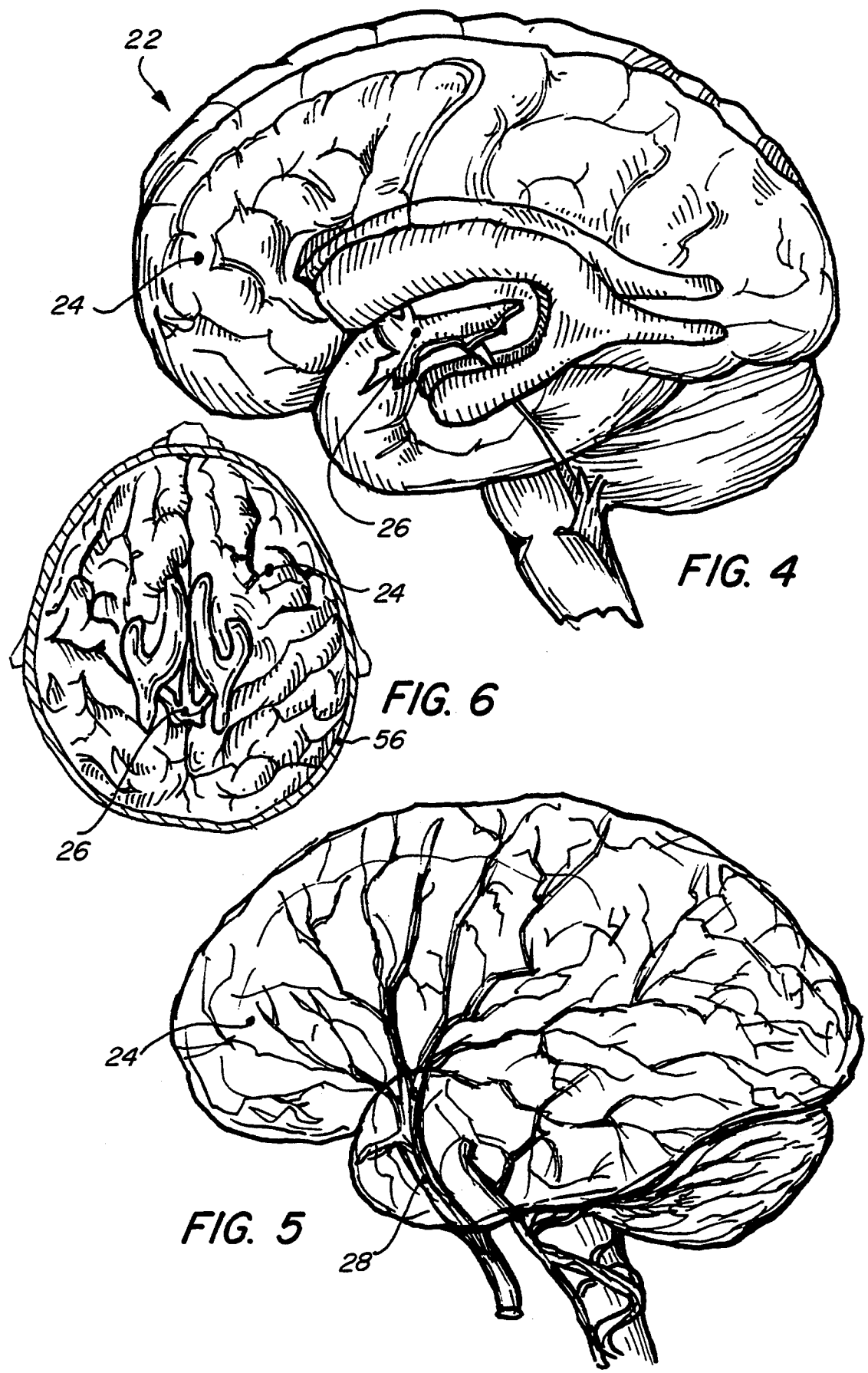

METHOD AND APPARATUS FOR NON-INVASIVELY DERIVING AND INDICATING OF DYNAMIC CHARACTERISTICS OF THE HUMAN AND ANIMAL INTRACRANIAL MEDIA

FIELD OF THE INVENTION

This invention generally relates to a method and apparatus for non-invasively investigating an intracranial medium or some other physiological medium. More specifically, this invention relates to a method and apparatus for non-invasively deriving an indication of dynamic characteristics of cerebrovascular and intracranial blood pressure activity from a measurement of the travel times of ultrasonic pulses through the intracranial medium.

BACKGROUND OF THE INVENTION

The time dependence of the intracranial blood pressure and the cerebrovascular pulsatility are essential parameters for the autoregulation of brain blood circulation. The time dependencies of these parameters, such as the shape of the intracranial pressure pulses and their reactions to various tests (jugular veins compression, hyperventilation, retention or respiration, various pharmacological tests, etc.) indicate accurately the type of pathology. For that reason, in vivo dynamic intracranial blood pressure measurements are made in clinical practice.

But known measurement methods for that purpose are invasive. That means, it is imperative to trapan the human crane and implant a mechanical/electrical sensor for pressure measurement, see for example publications on these techniques: Richards R., Illingworth R., "A Single System of Intracranial Pressure Monitoring for Use by Non-Neurosurgeons", Intensive Care Med. 12 (1986), 325–327; Mohsenipour I., "Modified Epidural Measurement of the Intracranial Pressure", Zentralblatt for Neurochirurgie (VEB Johann) 50 (1989), 24–27.

Non-invasive ultrasonic Doppler blood velocity meters are known and used for diagnosing intracranial basal arteries, see U.S. Pat. No. 4,930,513, Jul. 26, 1990, entitled "Two Dimensional Processing of Pulsed Doppler Signals". Methods of ultrasound echoscopy are known. For example, in "Physical Principles of Medical Ultrasonics", Editor C. R. Hill, Ellis Horwood LEd. Publishers: A Division of John Wiley & Sons (1986), an ultrasonic technique is described for the production of images of structures within a body corresponding to a local value of ultrasound attenuation at a corresponding point in the body. These methods have recently been described in U.S. Pat. No. 4,389,892 to Jonathan Ophir and Nabil Maklad and in U.S. Pat. No. 4,676,250 to Casper W. Barnes.

However, ultrasonic Doppler or echoscopic methods do not allow one to get information on dynamic characteristics of cerebrovascular pulsations of a human intracranial medium such as their time dependencies.

SUMMARY OF THE INVENTION

With an ultrasonic investigation method and apparatus in accordance with the invention, it is possible to determine the dynamic characteristics of cerebrovascular pulsatility of the human intracranial medium directly and non-invasively from the transit time values of elastic waves pulses which have been propagated through the medium under investigation.

One non-invasive technique in accordance with the invention for deriving indications of the dynamic behavior of the brain medium employs the use of at least one pair of ultrasonic transducers. These are positioned to inject, non-invasively, fast-rising and short ultrasonic acoustic pulses along a path selected to intersect a desired region of the intracranial medium, such as found along a path which intersects primarily brain tissue, or a cerebroventricle or a basal artery.

The acoustic pulses from one transducer are detected by the other in a precise repeatable manner so as to produce transit travel time signals representative of the length of the path and, for example, reflect path changes attributable to diameter changes in a basal arterial blood vessel or attributable to dimensional changes in the cerebroventricles.

We have found from experiments that, when the brain volume decreases, i.e. the brain is compressed, the changes in the acoustic velocity, $\Delta c(t)$, of ultrasonic pulses is directly proportional to the incremental change in the intracraniumpressure, $\Delta p$. This means that $\Delta c(t)$ depends upon $\Delta p(t)$.

Since the intracranium pressure $P_{IC}(t)$ can be expressed as the sum of an average component, $P^{(\phi)}{}_{IC}$, and a variable component $\Delta p(t)$, then it can be shown that by measuring the travel time accurately one can obtain an evaluation of the change in the intracranium pressure. Thus by obtaining a measurement of the changes in the travel time due to the effect of cardiac pulses on different portions of the brain, an indication of the pressure changes in that portion can be determined.

One technique for producing the transit travel time signals involves activating each transmitting transducer in response to a detected pulse. In such case an accurate measurement of the detected pulse repetition frequency, f, enables one to extract the changes in the frequency, $\Delta f$, and thus an indication of the change in pressure, $\Delta p$, of the intracranium medium through which the acoustic pulses travelled.

In another technique, each transmitting transducer is activated in response to a clock pulse from a highly stable clock source. In such case the elapsed time between the generation of the acoustic transmitting pulse and the detection of that pulse represents the travel time. The repetition period of the train of detected pulses depends on the change in intracranium pressure.

The transit travel time signals are processed in a manner whereby the portion reflecting path length changes due to diameter changes of a basal artery or pulsation of a brain ventricle can be isolated and separated to provide an indication of the dynamic behavior of the selected portion of the intracranial medium.

One technique in accordance with the invention for isolating the small changes in transit travel times involves repeatedly exciting a transmitting ultrasonic transducer coupled to an exterior portion of the cranium and deriving transit travel time signals from another similarly coupled ultrasonic transducer. The latter transducer may be located on an opposite side of the cranium or on the same side. The intracranium path or axis along which the acoustic pulses travel is preferably selected to intersect particular regions such as the ventricles, basal arteries, or mainly brain tissue.

The travel time signals recur at a rapid rate and are applied to a mixer to modulate a higher frequency signal. Since the transmitted ultrasonic pulse and the detected pulse have very sharp rise times, the travel time signals contain higher harmonics which appear in the frequency spectrum at the input and output of the mixer.

The modulated travel time signals are then applied to a bandpass filter to extract a desired high harmonic whose frequency is well above a significant portion of the noise spectrum. The high harmonic is then downshifted in frequency within a mixer whose low frequency output is isolated with a low pass filter to produce a parameter signal. The parameter signal is representative of a dynamic characteristic of the intracranium medium through which the ultrasonic pulses passed. This can be a cerebral basal artery or ventricles of the brain or brain tissue depending upon the placements of the transducers.

Further processing of the parameter signal can provide a signal that is proportional to or representative of the time variations or changes in the pressure inside cerebral arteries and when combined with ultrasonic measurements of other cerebral regions can yield signals indicative of the time dependencies of the diameter of a basal artery and a cerebral ventricle.

With a technique in accordance with the invention, an indication of the intracranial pressure (ICP), cerebral blood flow (CBF) as well as brain tissue elasticity changes and cerebral ventricle changes as a function of time can be obtained in a fast non-invasive manner. With measurements made in accordance with the invention, the treatment of certain brain disorders such as intracranial hypertension, improper cerebral blood circulation can be enhanced. Changes in the cerebral blood flow (CBF) and metabolic activity of the brain with the onset of aging and dementia can be monitored and evaluated.

It can be possible, in case of severe brain lesions to evaluate cerebral vasospasms and very fast changes in the intracranial pressure (ICP).

The monitoring and evaluation of CBF and ICP changes during a migraine attack and the effectiveness of its treatment is made possible. Such non-invasive technique is of particular value for children patients.

Information about the dynamic behavior of CBF, ICP and brain tissue can be invaluable for patients suffering from headaches, hydrocephalus, and disorders of cerebral blood circulation. The technique can provide an early diagnosis of brain death, an important diagnosis for transplant surgery.

It is, therefore, one object of the invention to provide a technique for non-invasively investigating the intracranium medium and derive signals indicative of dynamic characteristics of the intracranium medium, such as the intracranium pressure, cerebral arteries and ventricles. It is a further object of the invention to provide an ultrasonic method and apparatus for deriving indications of such intracranium characteristics from a measurement of the travel time of acoustic pulses injected in a non-invasive manner into the intracranium medium.

These and other objects and advantages of the invention can be derived from the following detailed description of several embodiments of the invention as shown in the drawings.

BRIEF DESCRIPTION OF THE DRAWINGS

FIGS. 4, 5 and 6 are views of the intracranium medium of a person and respectively are a lateral or side view, a median sagittal section view and a top view;

FIGS. 7, 8 and 9 are time-aligned curves of physiological characteristics wherein FIG. 7 represents intracranial pressure pulses, $P_{oc}(t)$, caused by cardiac pulses, FIG. 8 is a representation of a cerebral basal artery, and FIG. 9 is a representation of a cerebrospinal fluid bed such as the third ventricle of the brain;

FIG. 13b is plot of velocity measurements in opposite directions and the averaging of these in the manner described in connection with FIG. 13a;

FIG. 16 is a timing diagram of various signals generated in the apparatus of FIG. 13a;

DETAILED DESCRIPTION OF THE DRAWINGS

Figure 1:
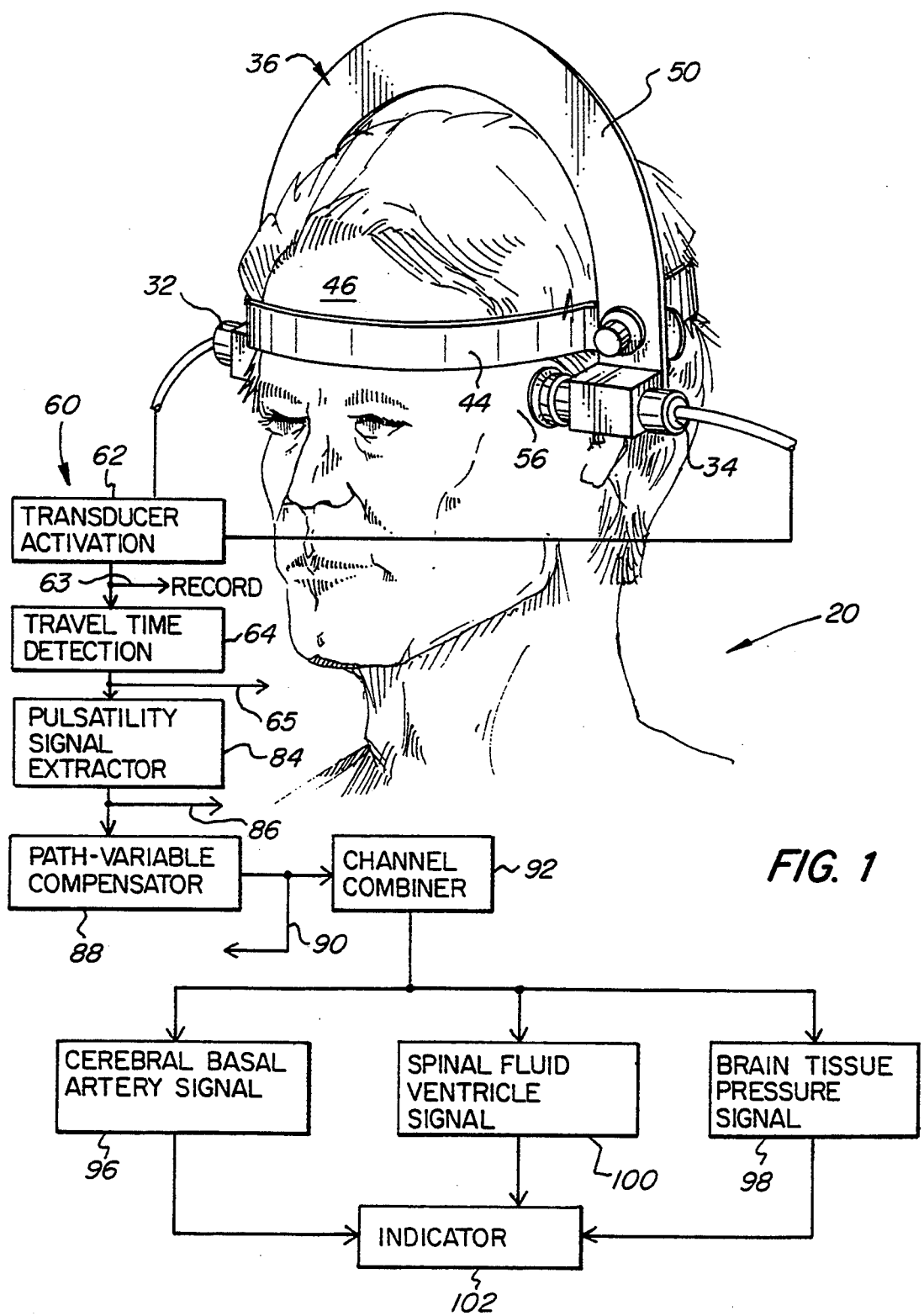
FIG. 1 is a perspective view of one ultrasonic apparatus in accordance with the invention as used on person's head.
Figure 2:
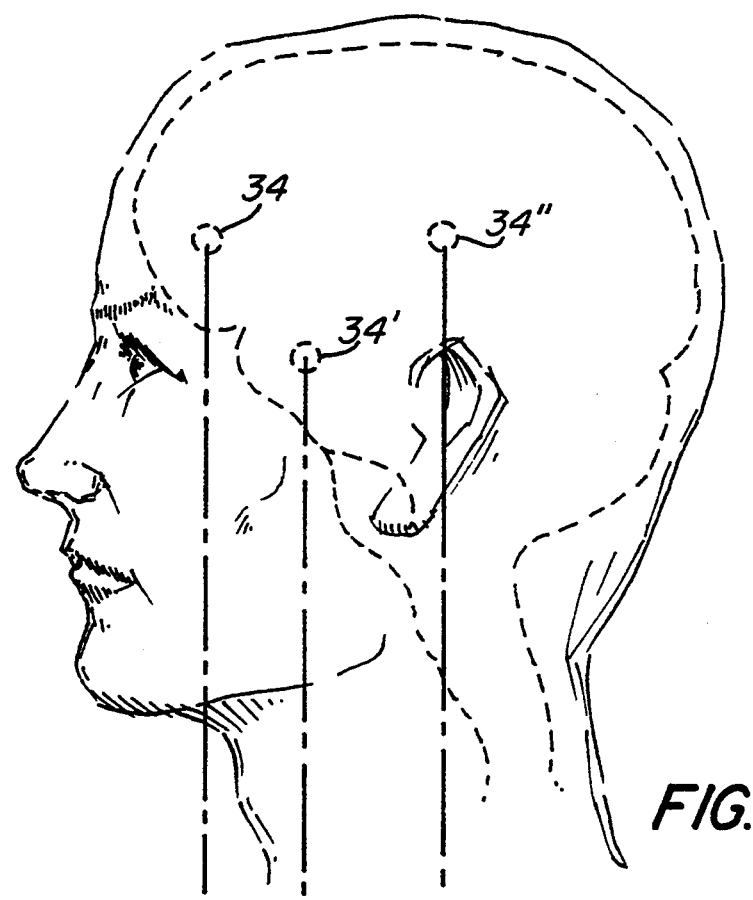
FIGS. 2 and 3 are respectively side and top views of a person's head and path lines for ultrasonic transducers and pulses used to investigate the intracranium medium.
Figure 3:
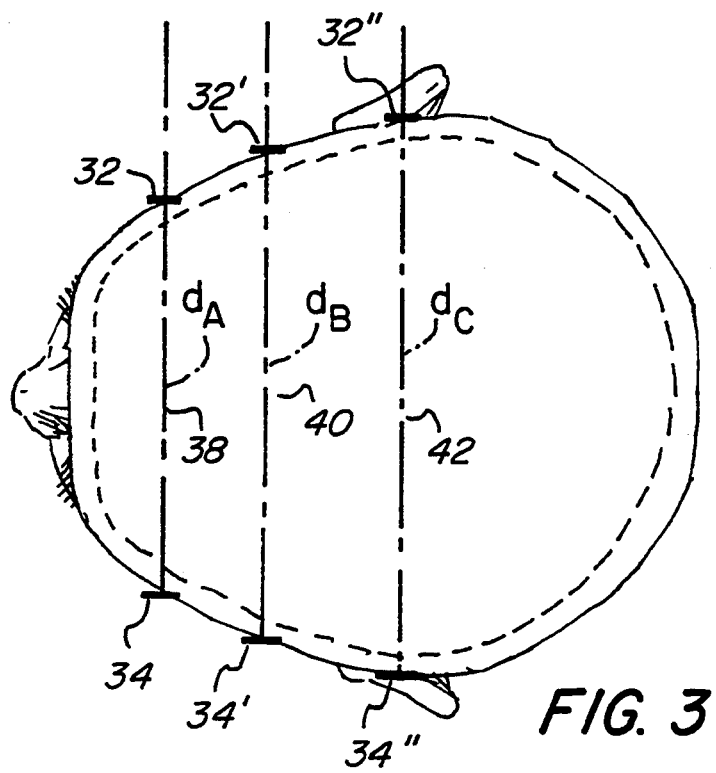

With reference to FIGS. 1-3 a system 20 is shown for deriving an indication of one or more dynamic characteristics of the intracranium medium 22. The characteristic can be the time dependence of the intracranium pressure of brain tissue such as at 24 in FIGS. 4-6, or the cerebrovascular pulsatility of the cerebrospinal fluid bed at 26 in a ventricle as shown in FIGS. 4 and 6, or a cerebral basal artery at 28 in FIG. 5. Other characteristic whose variation affects the transit travel time of an ultrasonic pulse passing through the brain 22 can be measured.

System 20 employs at least one pair of ultrasonic transducers 32, 34, which are mounted on a frame assembly 36 that can be mounted on a person's head. The frame assembly 36 can be formed in a variety of ways, however, it is essential that the transducers 32, 34 are held in a stable position once they have been aligned along a desired path such as 38, 40 or 42, see FIG. 3, in the brain 22.

Figure 22:
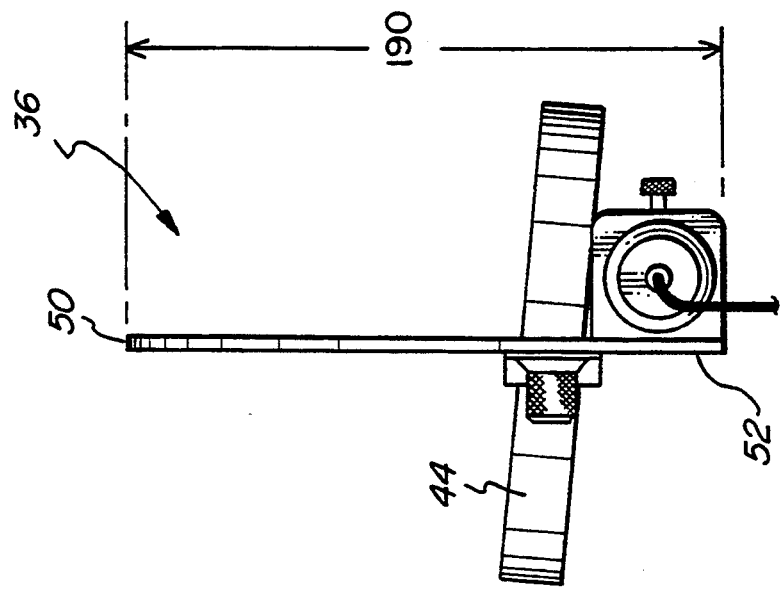
FIG. 22 is a side view of the frame of FIG. 21.
Figure 21:
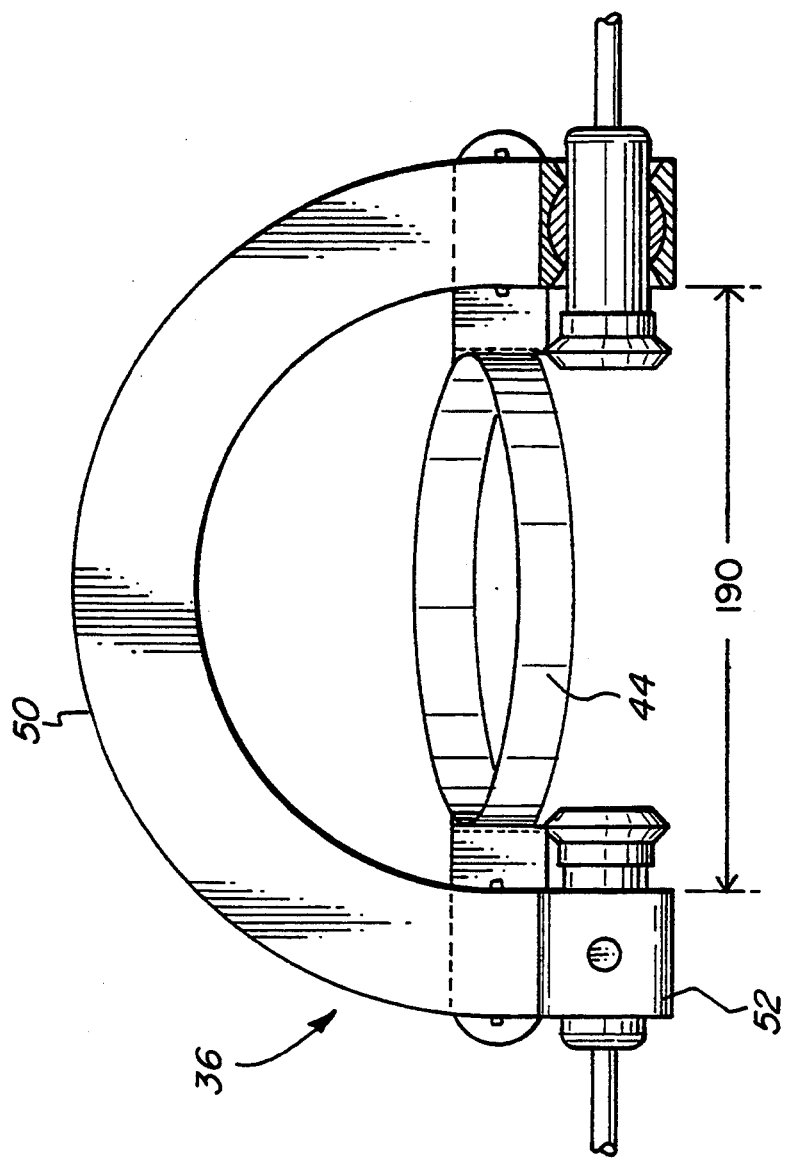
FIG. 21 is front view in elevation of a frame used to mount and support transducers on a person's head.

Frame 36, therefore, as more particularly shown in FIGS. 1, 21 and 22, is formed of a flexible band 44 that can be adjusted to fit over a person's forehead 46. Band 44 can be made with a suitable Velcro type fastener that is adjusted to fit snugly and comfortably over the forehead 46 and prevent a downward slipping of frame 36. A rigid metal bar 50 adjustably attaches to band 44 and supports transducers 32,34 at ends 52. The transducers can be moved towards and away from the outer cranium 56 so as to be able to fit at different positions along the head and with different persons. The transducers 32,34 can be fixed in place with sufficient pressure to enable ultrasonic coupling of pulses into the cranium through a suitable ultrasonic coupling gel. Frame 36 can be made generally similar to well known frames as are used in sonic Doppler investigations of the brain.

In the embodiment of FIG. 1 a single pair of ultrasonic transducers 32,34 is used to investigate, for example either one or successively one of the brain paths 38, 40, or 42. This involves the appropriate alignment, see FIGS. 2 and 3, of the transducers 32, 34 to determine, for example, pulsations in the brain tissue pressure, path 38, or pulsatility of spinal fluid in a brain ventricle, path 42, or the pulsations in a basal artery, path 40. Alternatively a multiple of transducer pairs 32-34, 32'-34', 32"-34" could be simultaneously employed and aligned along these respective or other brain paths.

In the embodiment shown in FIG. 1 a technique 60 in accordance with the invention is shown wherein at 62 a suitable network is shown for actuating transducers 32,34. One ultrasonic transducer is driven by an electric pulse to generate an acoustic pulse that is transmitted into the brain, while the other transducer serves as the detector of an incident acoustic pulse after it has traversed a path in the brain.

Figure 7:
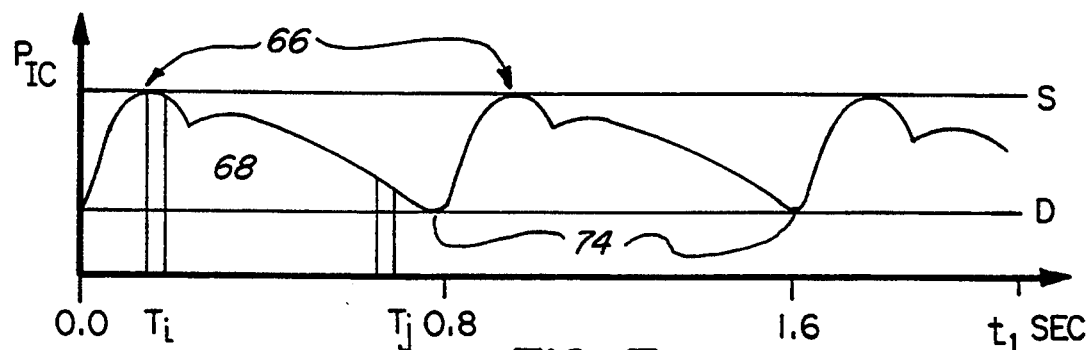
Figure 8:
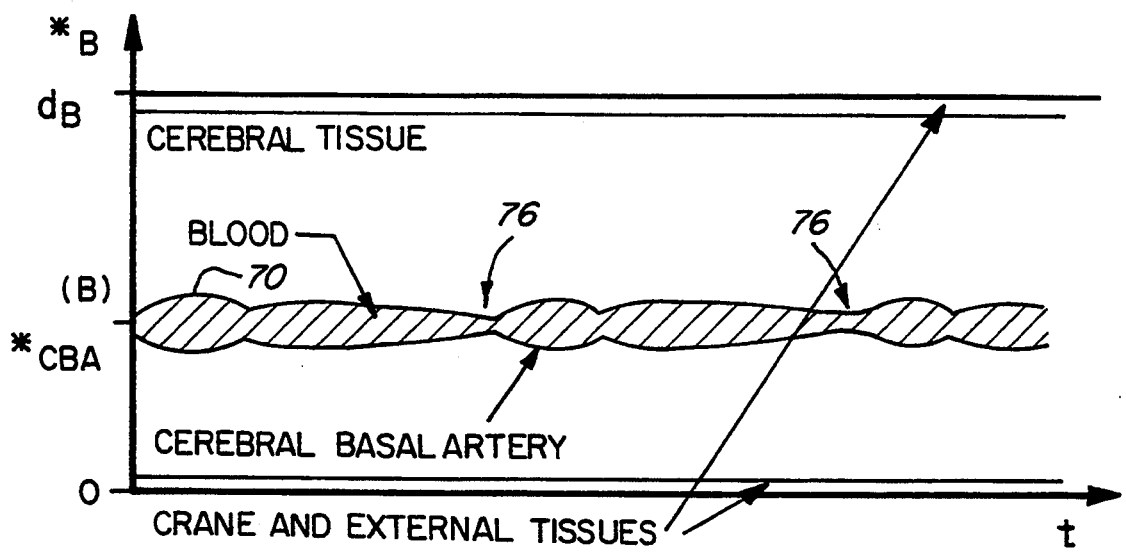
Figure 9:
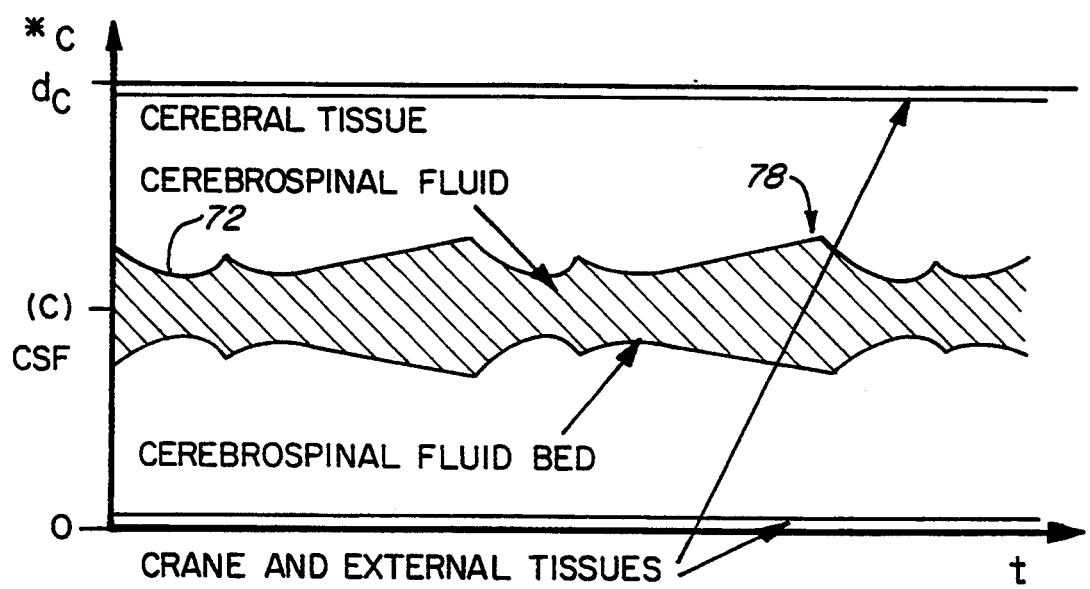

At 64 the time for the acoustic pulse to traverse the axis or path in the brain is determined using a transit travel time measuring technique. The transit travel time, $\tau(t)$, then includes the variations encountered along the travel path in the brain. For example, with reference to FIGS. 7, 8 and 9 the occurrence of a systolic event at 66 of the cardiac pulse 68 is accompanied by a widening of the basal artery at 70 in FIG. 8 and a narrowing of the cerebral fluid bed at 72 in FIG. 9.

Transit time or travel time, pulses or signals, as such terms are used herein thus include those signals as detected and received with the embodiments as long as such signals include detectable variations attributable to time-dependent changes in a physical body such as the intracranial medium.

The enlargement of the basal artery due to the presence of a systolic high blood pressure cardiac pulse will cause a slight delay in the transit travel time when the acoustic path traverses the basal artery at 70 and a slight reduction of the travel time when the acoustic path crosses the spinal fluid bed at 72. Correspondingly, the occurrence of a diastolic event at 74 enables a narrowing of the basal artery at 76 and a widening of the spinal fluid bed at 78. This would result in a lengthening of the travel time at 78 and a shortening at 76. It is these transit time variations that the invention measures.

Figure 10A:
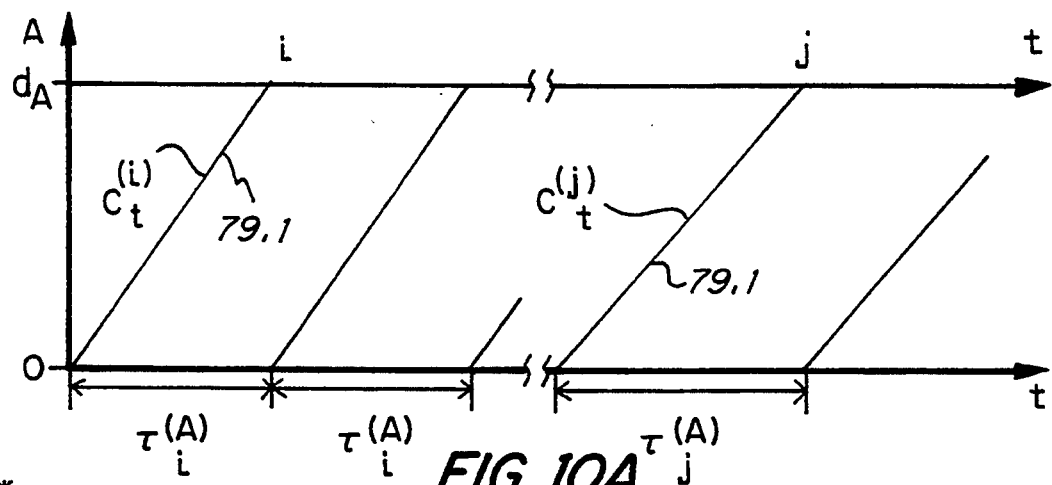
FIGS. 10a, 10b, and 10c are idealized timing diagrams of acoustic pulse travel paths through respectively primarily brain tissue, a brain region containing a basal artery, and a brain region containing a cerebro ventricle.
Figure 10B:
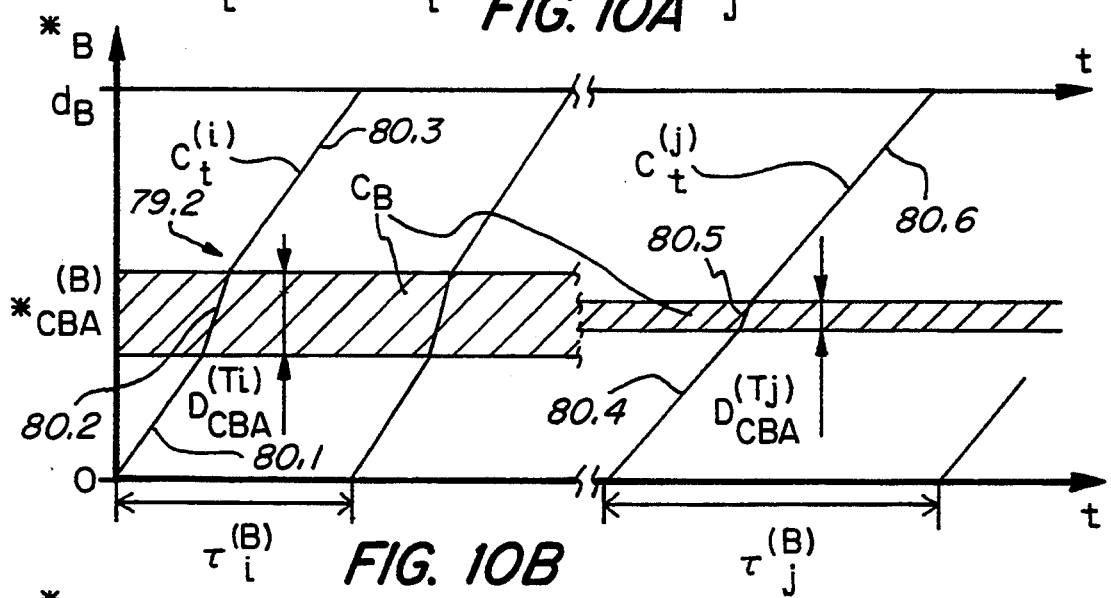
Figure 10C:
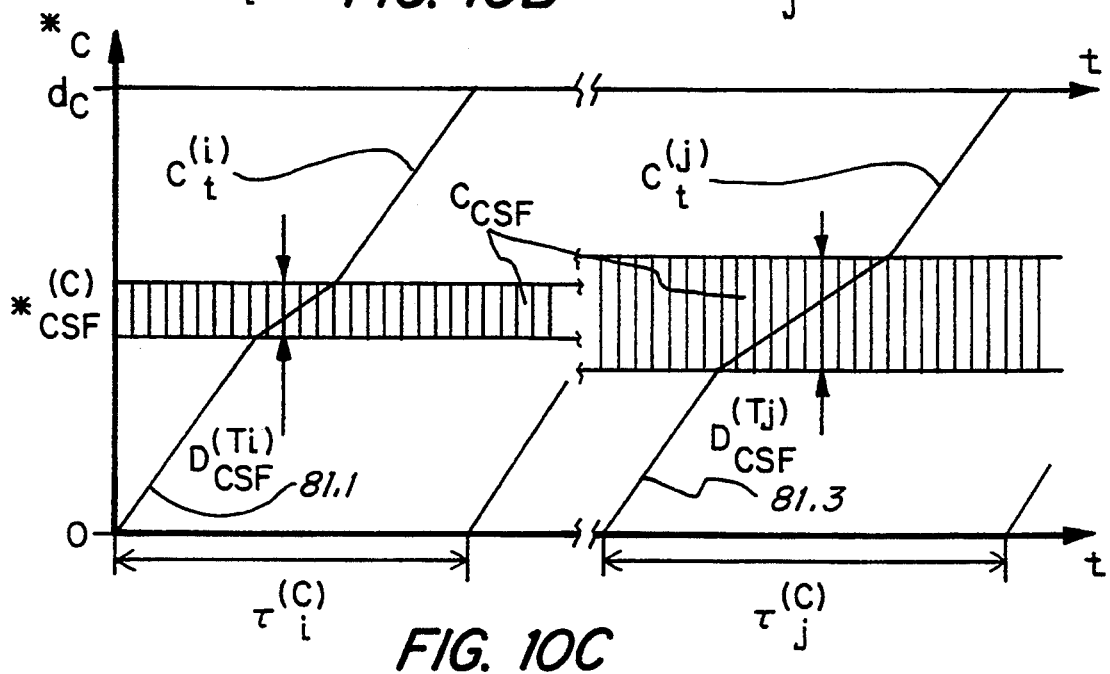

Brain tissue is compressible, but the blood and cerebrospinal fluid are almost incompressible. FIGS. 10a, 10b and 10c respectively illustrate in a schematic manner the dynamic reactions of brain tissue, a basal artery and a cerebrospinal fluid ventricle in response to cardiac pulses. These Figures show how the changes in the brain pressure, $P_{IC}$, affect the velocities, c, and thus the travel times, $\tau$, of acoustic pulses along paths, $d_A$, $d_B$, $d_C$, corresponding to paths 38, 40 and 42 in FIG. 3.

In FIG. 10a, which shows the velocities, $c_t$, curves 79.1, of acoustic pulses through primarily brain tissue, the slopes of the curves 79 1, $c^{(i)}$ during systolic events is higher than for curves, $c^{(j)}$, during diastolic events. The travel times $\tau$ vary correspondingly.

In FIG. 10b the acoustic velocity curve 79.2 is a combination of the velocity through brain tissue, segment 80.1, a basal artery having a diameter $D_{CBA}$, segment 80.2, and another brain tissue segment 80.3. During a systolic event the slopes of the segments 80.1 and 80.3 are different from those during a diastolic event. However, the slopes of the segments passing through a basal artery, such as segments 80.2 and 80.5 remain the same because of the incompressibility of the blood.

FIG. 10c illustrates velocity curves 81.1 and 81.3 with a similar behavior as the curves 79.1 and 79.2 in FIG. 10b and illustrate that when the acoustic paths intersect either a basal artery or a ventricle, acoustic travel times vary primarily as a function of the changes in pressure brought on from cardiac pulses.

Figure 11:
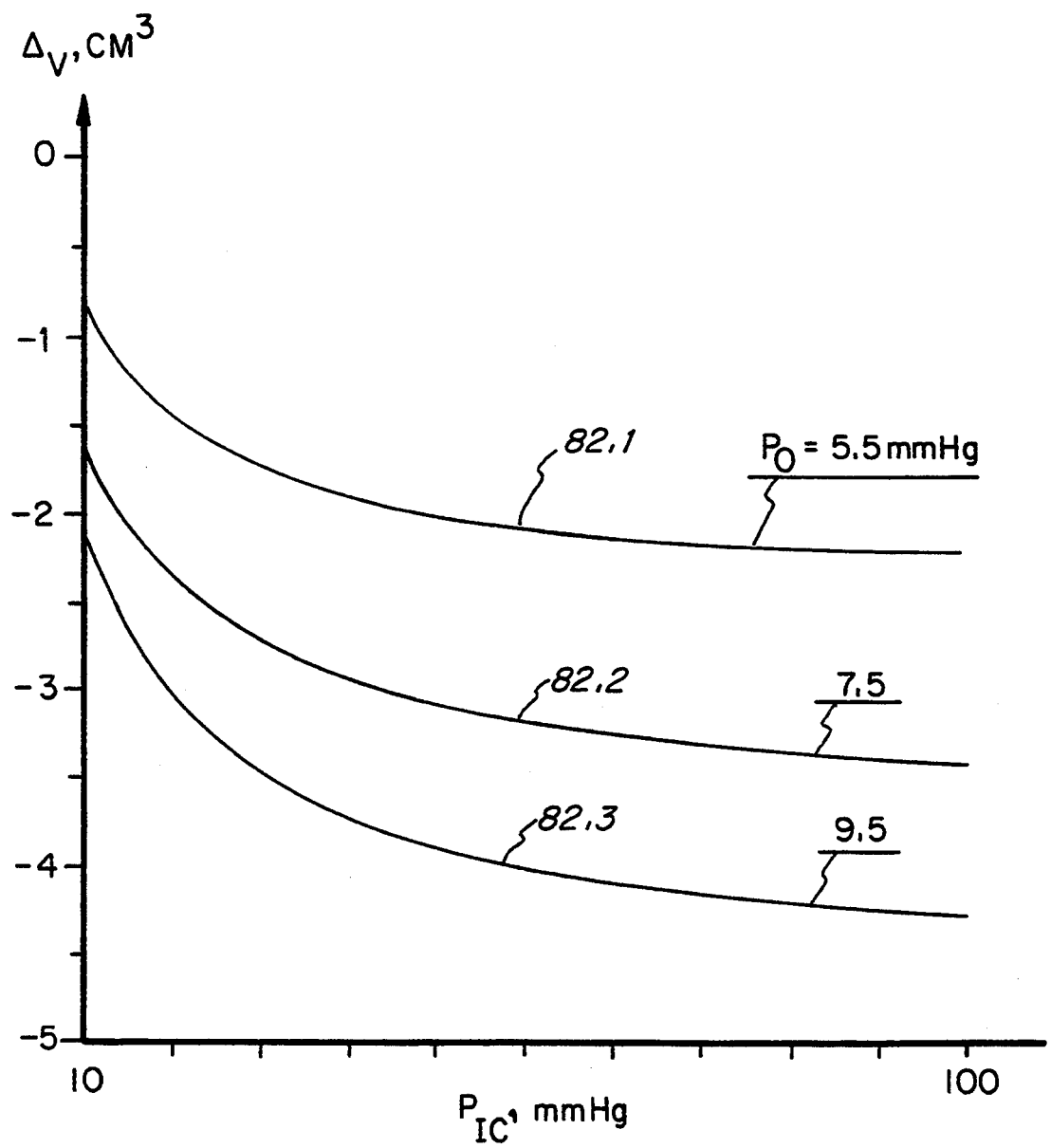
FIG. 11 is a plot of curves showing variations of brain volume and brain pressure.

The curves 82.1-82.3 in FIG. 11 illustrate the dependency of intracranium brain pressure $P_{IC}$ as a function of brain volume for different average pressures $P_0$. At the higher brain pressures the brain volume remains substantially constant. The measurements of the variations in the acoustic travel times depend upon the changes in the brain pressure $\Delta_P$ along the acoustic path.

Hence, at 84 in FIG. 1 the pulsatility of the transit travel time signals are extracted to produce a parameter signal on line 86, which is indicative of the pulsatility of the basal artery or such other characteristic of a brain segment through which the acoustic pulses from the transducers 32, 34 travel.

It is desirable to exclude as much noise as possible from the measurements of transit travel times since their accuracy must be of the order of one part in $10^7$ or better. Hence, at 88 appropriate steps are taken to remove deviations attributable to factors such as when an artery moves or when the geometry of the artery relative to the path of the acoustic pulses introduces removable errors. These steps at 88 thus involve alternating the operation of the transducers so that during one interval one transducer acts as the transmitter while in the next interval the other transducer acts as the transmitter. The resulting travel time measurements $\tau_o$ from alternate transducers are combined and averaged at 88 to produce an improved parameter signal at output line 90 that can be used or recorded.

The extraction of the pulsatility or time dependence parameter from the travel time signal preferably is carried out by transforming the travel time signal to the frequency domain. The parameter signal is then derived from a desired pass band that lies well above the low frequency noise spectrum. Improved accuracy can be obtained by selecting several pass bands and then combining, such as by averaging, the parameter signals derived from different frequency channels at 92.

With the technique 20 signals representative of the pulsatility of the cerebral basal artery diameter at 96, the pressure of the brain tissue at 98 and the time dependency of the width of the spinal fluid ventricle at 100 can be obtained. These signals can then be indicated at 102 such as by displaying them on a video display or on a chart recorder or recorded in memory for further analysis or future display.

It should be noted that the technique 20 can be carried out after the transit travel time signals or detected acoustic pulses, together with their respective harmonics, have been recorded on a wideband recording medium. The acquired data, from which the invention can derive a parameter signal representative of a time dependency of a portion of the intracranial medium, can thus be analyzed in real-time as the ultrasonic transducers are activated or at a later time by recording at 63 received pulses from the transducers or the transit travel times at 65.

With reference to FIGS. 13a, 13b, 14, 15, and 16, a more detailed view of a system and method in accordance with the invention to measure and derive a value of a characteristic of the intracranium medium is shown. Ultrasonic transducers 32, 34 are mounted externally to a head with a device 36 as shown in FIG. 1 but deleted for clarity. The distance d between transducers 32, 34 is a function of their location and thus the path through the intracranium medium 22.

Measurement of the transit time between transducers 32, 34 is accurately done with a sharply rising and short excitation voltage pulse 110 (see FIG. 16) derived from the leading edge of a pulse 126 generated from a zero crossover detection network 127 inside a receiver 124. Such crossover detection networks are well known. The pulse 110 is of the order of a tenth of a microsecond long and causes the generation of a short burst 114 from a transmitter 116 at a center frequency of five MegaHerz. The 5 MHz bursts is about two and a half microseconds in duration with most of its energy being within the first microsecond as illustrated. The short burst 114 is passed through a commutator 118, which acts as a reversing switch, to transducer 34.

Figure 16:
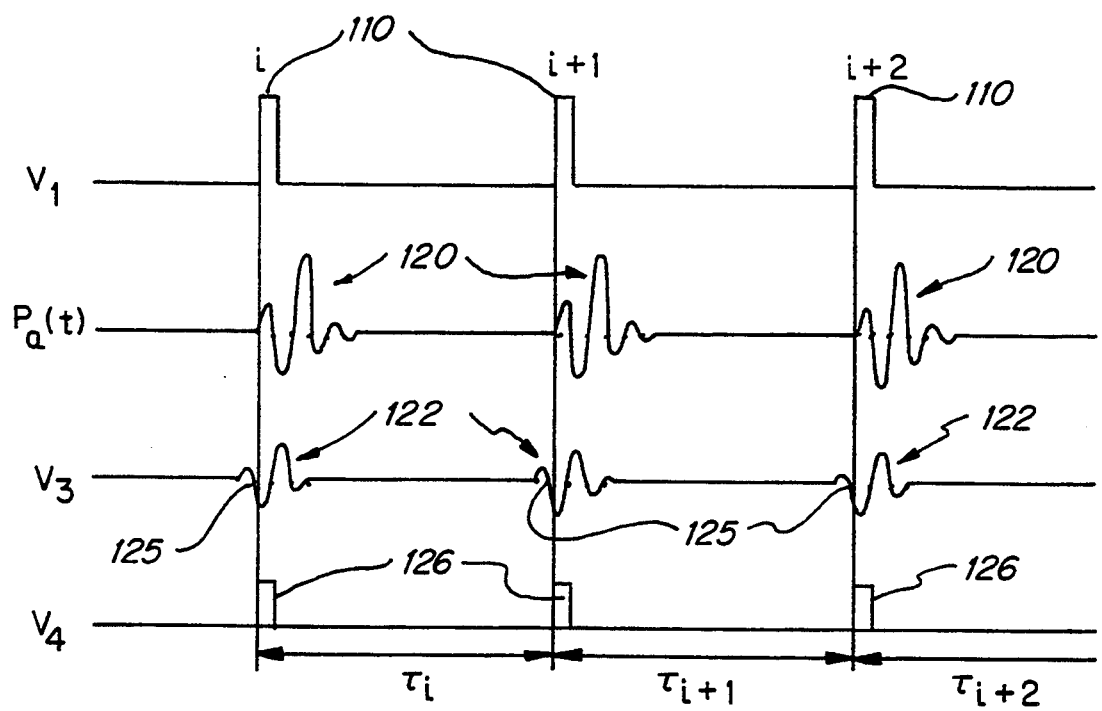

The transducer 34 responds with a very short acoustic pulse 120, see FIG. 16, that is coupled through the outer cranium and into the intracranium medium 22. The acoustic pulse 120 is transformed by transducer 32 to an electrical signal 122, see FIGS. 15 and 16, that, after passing through the reversing switch 118 is applied to a receiver detector 124.

The receiver detector amplifies signal 122 and includes a well known crossover network 127 with which the first zero crossover 125, see FIG. 16, of signal 122 is detected and causes an output pulse 126 representative of when the first signal from the transmitting transducer was detected. Pulse 126 has a very fast rise time and preferably is of very short duration, of the order of about a nanosecond.

The rising leading edge of pulse 126 reactivates transmitter 116 to repeat the process as described. Except, however, that the output 130 from a pulse generator 112 is used to reverse switch 118 periodically at time intervals of $T_D$ typically of the order of a tenth of a second. A reversal of switch 118 sends the reactivated transmission from high frequency burst transmitter 116 to transducer 32 and the detected acoustic pulse from transducer 34 to receiver 124. The effect of this reversing is illustrated in FIG. 13b. Switch 118 can be a semiconductor switch.

FIG. 13b is illustrative of the averaging effect obtained by alternating the direction of the travel time measurements with the reversal switch 118. At 131.1 is a curve of each of the actual measurements of the velocity $\Delta c(t)$ in the opposite directions, while curve 131.2 shows the effect of averaging the measurements in curve 131.1.

The repetition frequency of the interval pulse signals generated at output 132 of receiver 124 is representative of the inverse of the acoustic travel time $\tau_\phi$ through the intracranium medium. The frequency of these pulses includes an average frequency $f_\phi$ plus a variable portion $\Delta f(t)$ attributable to variations introduced from changes along the path d in brain medium 22. The use of the subscripts $\phi$ and 0 herein mean the same, namely the mean value.

Because of the brief nature of the travel time pulses on line 132, they contain many higher harmonics. These harmonics extend very high in frequency and their amplitudes fall off with frequency at a typical rate determined by the function sinx/z until the amplitudes approach a first minimum level at about one gigahertz if the width of pulses 126 on line 132, see FIG. 16, is about one nanosecond.

The travel time signals on line 132 are applied to a mixer 136 to amplitude modulate a coherent frequency signal $f_1$ of the order of about 8 MHz on line 138 from a frequency signal generator 140. The output 142 from mixer 136 then includes the higher harmonics 143.1-143.J, but centered at elevated frequencies at intervals separated by whole integer multiples of the average frequency $f_\phi$.

A first processing channel 146 operating in the frequency domain is used to extract the variable portion of the travel time signals. The output 142 of mixer 136 is applied to a bandpass filter 148 whose passband is sufficiently high in frequency so as to be above the low frequency spectrum of the noise on output 132. The frequency band $\Delta f_{(BPF)}$ of bandpass filter 148 is chosen so as to select a desired frequency modulated harmonic 143.J without distortion. This implies a frequency pass band for $\Delta f_{BFP}$ that is equal to or greater than $2F_{max}$ where $F_{max}$ is the frequency band of the spectrum of the selected harmonic 143.J.

Figure 13A:
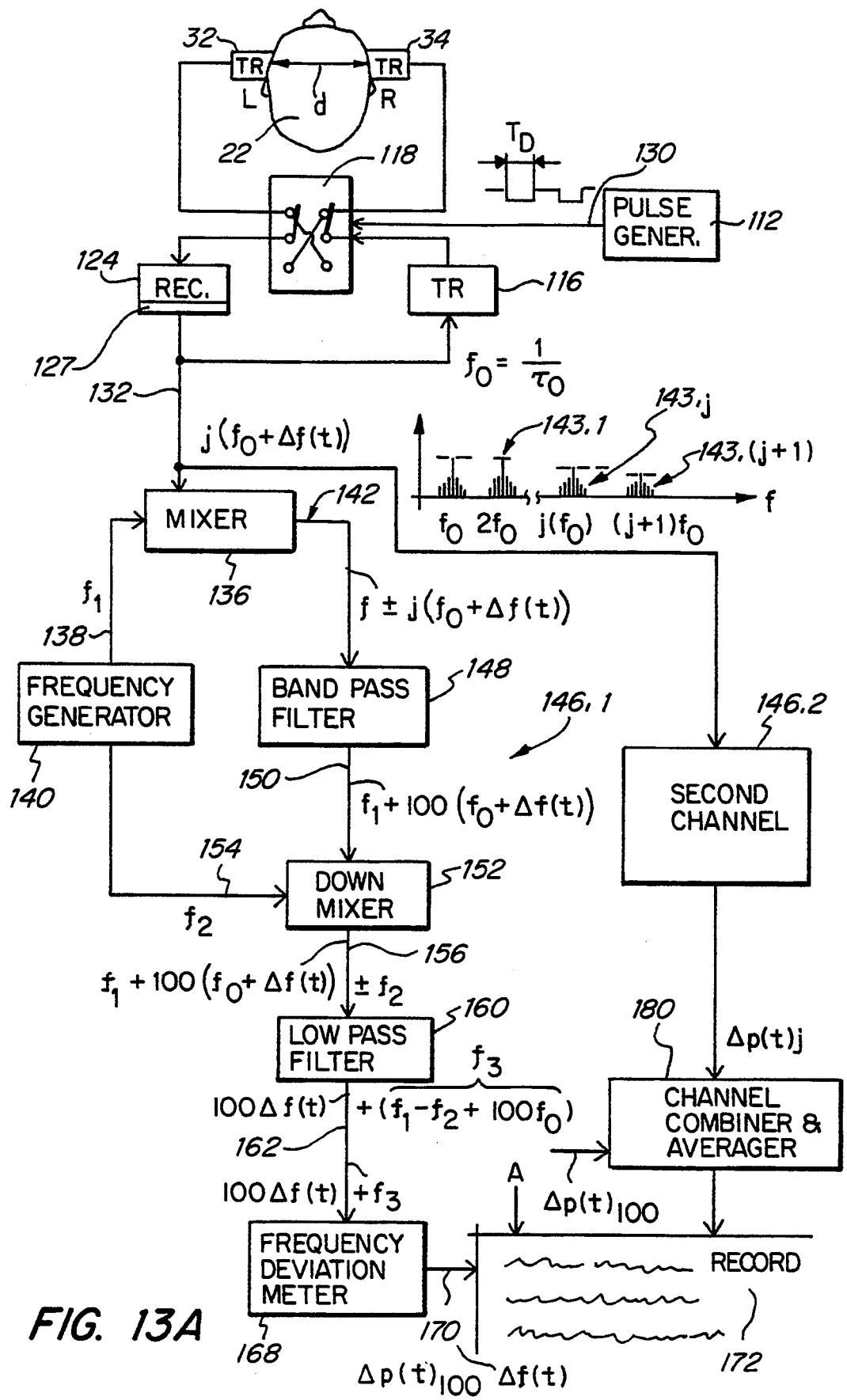
FIG. 13a is a schematic block diagram of one embodiment in accordance with the invention for producing a signal indicative of a dynamic characteristic of the intracranium medium.
Figure 13B:
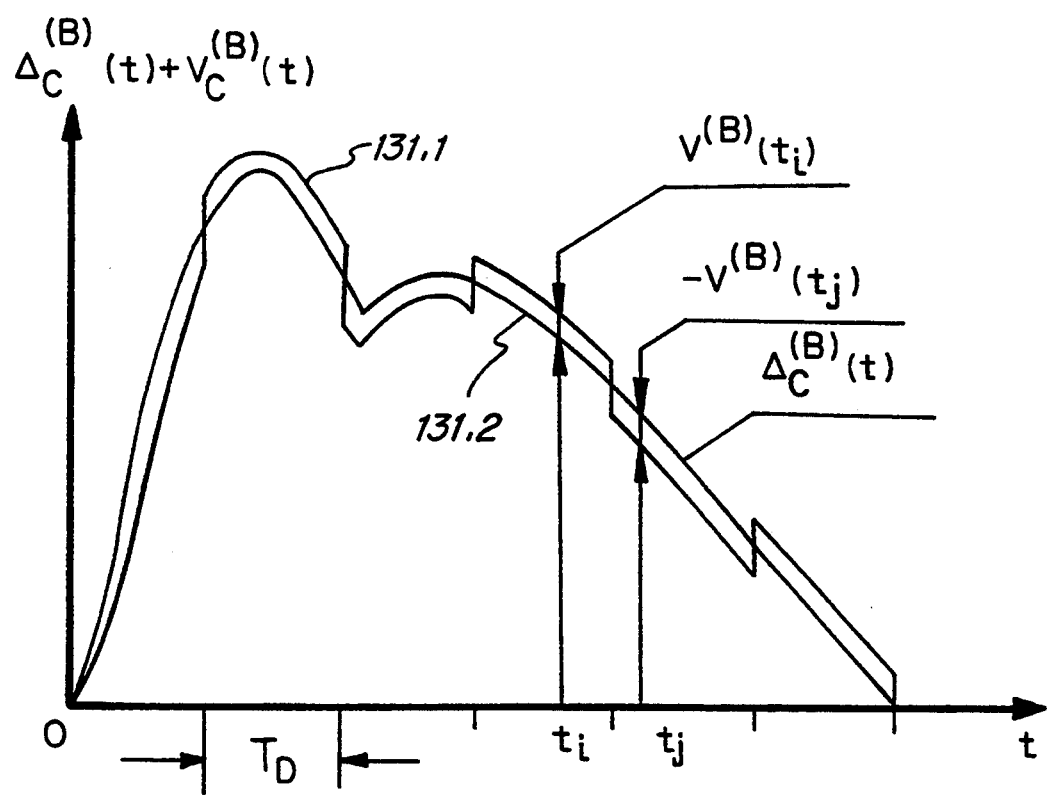
Figure 14:
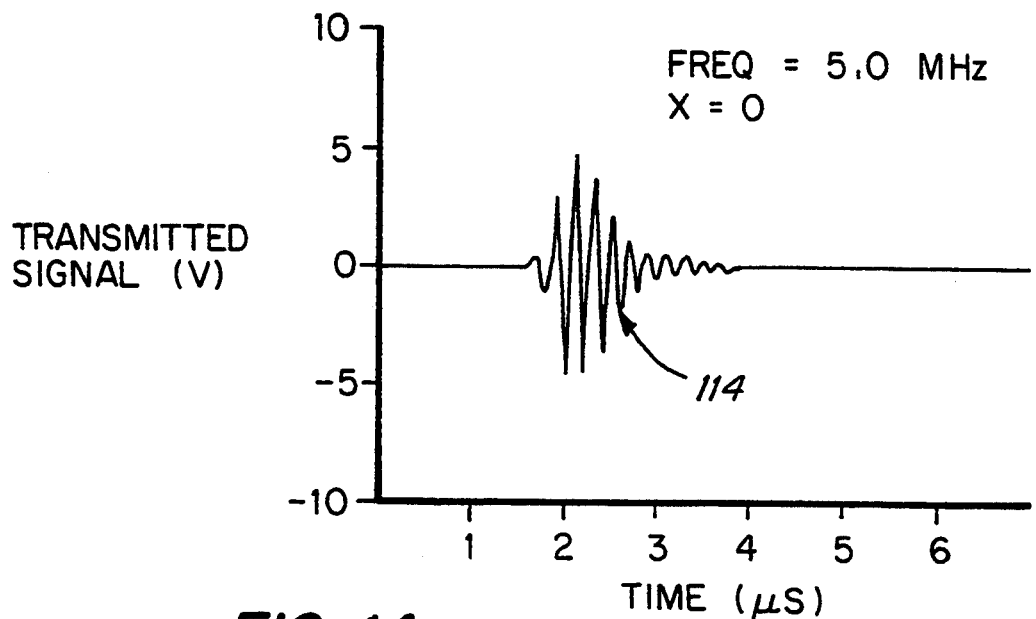
FIG. 14 is a timing diagram of an electrical representation of an acoustic pulse used to investigate the intracranium medium in accordance with the invention.
Figure 15:
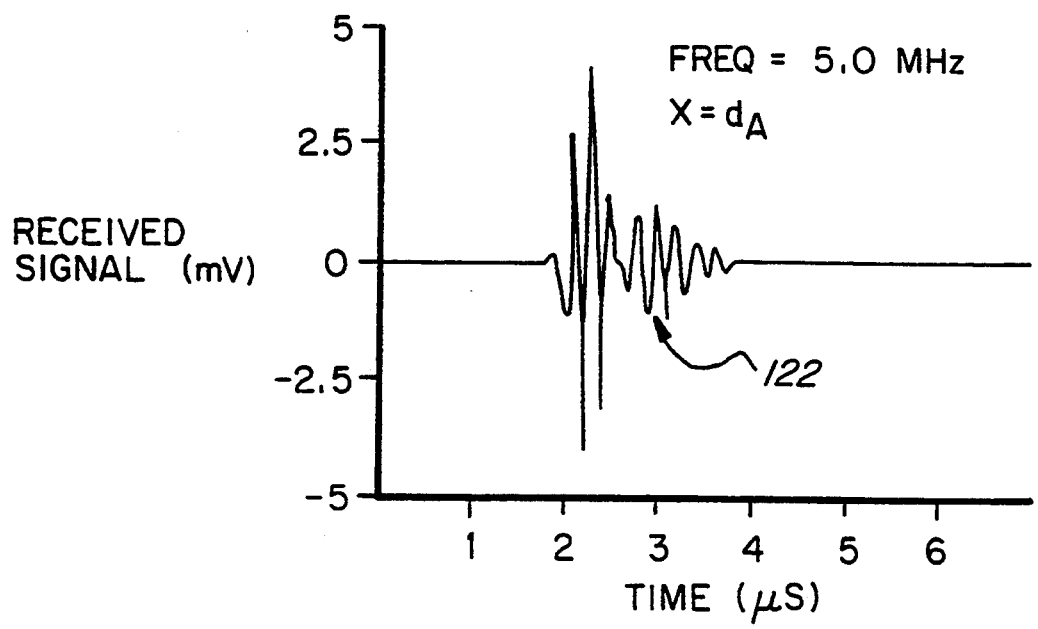
FIG. 15 is a timing diagram of the received acoustic signal after the acoustic pulse has traversed an intracranium medium.

In the example illustrated in FIG. 13a, the 100th harmonic is shown as selected, though different as well as higher harmonics 143.J could be chosen. The output 150 of bandpass filter 148 is, therefore, a combination of the harmonic, and is $f_1 + 100(f_\phi + \Delta f(t))$.

The output of the bandpass filter 148 is then down-shifted in frequency by applying the output on line 150 to a down-mixer 152 which is supplied on line 154 with a carrier frequency signal $f_2$ from generator 140 typically of the order of about 8.9995 MHz. The carrier signal $f_2$ is close in frequency to $f_1$, but sufficiently spaced in frequency to avoid low signal frequency modulation interference with the desired variable f(t). The output 156 of down mixer 152 carries the output modulation signal $f_1 + 100(f_\phi + \Delta f(t)) \pm f_2$.

The output on line 156 is then applied to a low pass filter 160 from which the low frequency components are supplied on output line 162, namely, $100\Delta f(t) + f_3$, where $f_3 = f_1 - f_2 + 100f_\phi$. Hence, the frequency of the parameter signal $\Delta f(t)$ is improved 100 times and as a result can be more easily extracted because $$\frac{100\Delta f(t)}{f_3} \gg \frac{\Delta f(t)}{f_0}.$$

The detectability of the parameter signal $\Delta f$ is substantially improved because in a practical situation the ratio of $$\frac{100\Delta f(t)}{f_3}$$

is more than 2000 times the ratio $$\frac{\Delta f(t)}{f_0}.$$

Typically $f_\phi$ is of the order of 10,000 Hz, a minimum value of $\Delta f$, $\Delta f_{min}$ typically is in the range from about $10^{-3}$ to about $10^{-4}$ Hz while $\Delta f$ is of the order of about 2.5 Hz and $f_3$ is of the order of about 500 Hz.

The value for $100\Delta f(t)$ is extracted at 168 with a frequency deviation meter 168 with which the deviation of $f_3$, namely $100\Delta f(t)$, can be obtained. This can be derived either by subtracting the value of $f_{3_0}$. Thus providing on output line 170 a parameter signal representative of the value $\Delta f(t)$. The scale value of 100 can be adjusted for because it is a known value. Note that the signal on line 162 can be recorded as an indication of the parameter value.

The value $f_3$ can be obtained by combining signals representative of $f_1$, $f_2$ and 100 times the average value $f_\phi$. The parameter signal can be indicated at 172 such as with a chart recorder or a printer or on a display or recorded in memory.

With the use of a single channel 146.1 the accuracy of the measurement of the parameter $\Delta_P(t)$ is of the order of about three percent. This accuracy can be improved with the use of one or more channels, each of which operates with a different harmonic present on output line 132 from receiver 124.

For example a channel 146.2 can be used to operate on the 200th harmonic to derive a measurement of the same parameter as channel 146.1. The measurements can then be combined at 180. The combiner 180 may for example average the measurements and record the result on the indicator 172. Accuracy is improved to a level of about two percent and by using additional channels further improvement in the measurement accuracy can be achieved.

Figure 12:
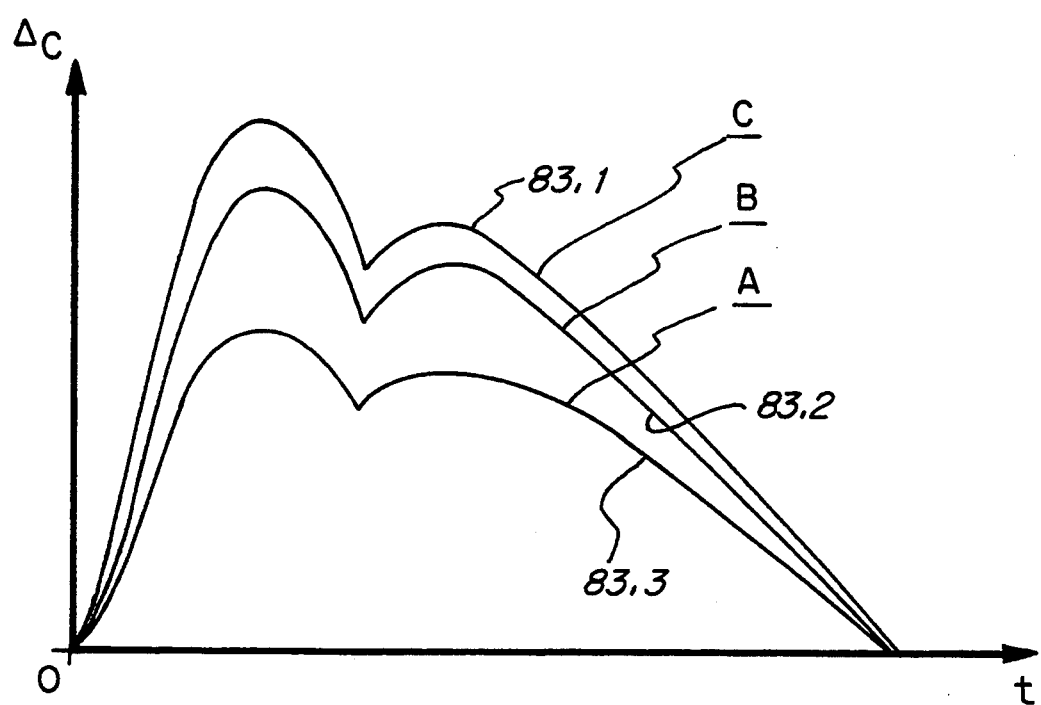
FIG. 12 is plot of different parameter time dependencies.

FIG. 12 illustrates curves 83.1-83.3, which are idealized representations of the incremental changes in the acoustic velocity measurements on a patient using the respective acoustic paths 38, 40, 42 shown in FIG. 3. These curves 83 are obtained from an idealized schematic view of the brain as shown in FIGS. 10a, 10b and 10c. From the latter Figures it is possible to calculate the time dependence of the pulsations of the basal artery diameter, $D_{BA}(t)$ using the relationship:

$$D_{BA}(t) = \frac{C_B\left[\frac{C_f(t)}{f^{(B)}(t)} - d_B\right]}{C_f(t) - C_B} \qquad (1)$$

where the subscript or superscript B identifies the path which intersects a basal artery.

In the same way it is possible to calculate the time dependency of the pulsation of the cerebrospinal fluid ventricle width $D_{CSF}(t)$ using the expression:

$$D_{CSF}(t) = \frac{C_{CSF}\left[\frac{C_f(t)}{f^{(C)}(t)} - d_C\right]}{C_f(t) - C_{CSF}} \qquad (2)$$

where the subscript or superscript C identifies the acoustic travel path which intersects a ventricle.

Since the values for the distances $d_a$, $d_b$, and $d_c$, between the transducers 32, 34 and the values for the acoustic velocities of the blood, $C_{BA}$, and spinal fluid, $C_{CSF}$, can be measured using conventional ultrasonic techniques, the invention provides a unique opportunity to evaluate dynamic parameters such as variations in, the pressure of brain tissue, $\Delta_P$, the diameter of a basal artery, $D_{BA}$, and the diameter of a brain ventricle, $D_{CSF}$.

Figure 20:
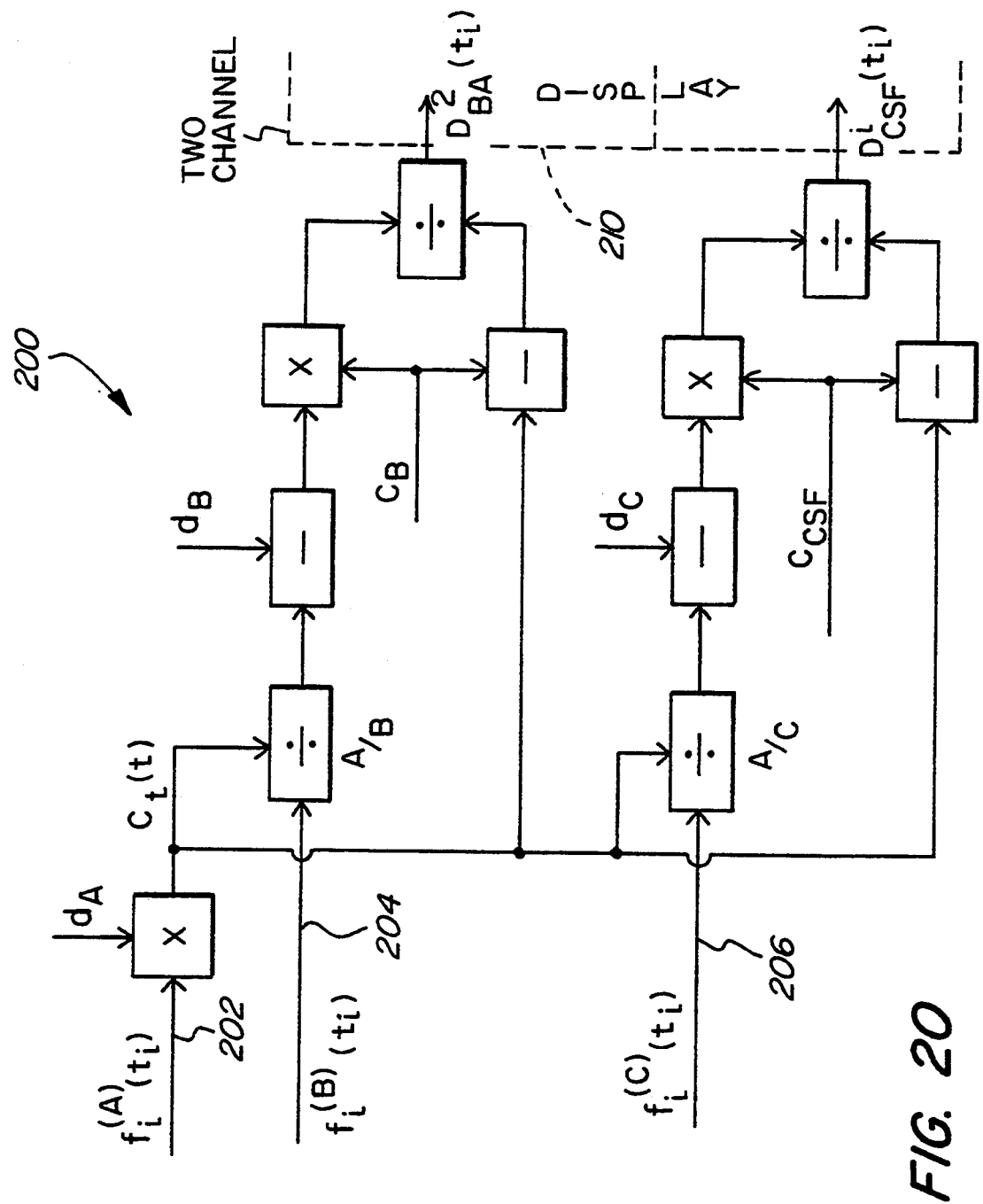
FIG. 20 is a block diagram view of an apparatus and method for combining various measurements of intracranium characteristics in accordance with the invention.

With reference to FIG. 20 a technique 200 is shown for deriving the values such as $D_{BA}(t)$, and $D_{CSF}(t)$, from measurements with an apparatus as shown in FIG. 13a. The technique 200 can be implemented with analog circuits or with an appropriately programmed computer which implement the expressions (1) and (2) above. Technique 200 relies upon the availability of measurements made, either simultaneously or sequentially, of the repetition frequency of pulses on a line 132 in FIG. 13a for the respective brain paths 38, 40 and 42, see FIG. 3. The repetition frequency signals are $f^A_i(t_i)$, for brain tissue, $f^B_1(t_1)$, for a basal artery intersecting path, and $f^c_i(t_i)$ for a cerebrospinal fluid intersecting path. Values of these frequency signals are applied on lines 202, 204, and 206 respectively in FIG. 20.

Values for the path distances $d_A$, $d_B$, and $d_C$ are obtained by combining ultrasonic measurements of the distances between transducers 32,34 along the respective paths 38,40, and 42 with published values for the acoustic velocities through spinal fluid, $C_{csf}$, brain tissue, $C_t$, and blood, $C_b$, see "Physical Principles of Medical Ultrasonics", edited by C. R. Hill and published in 1986 by Ellis Horwood Ltd., a division of Wiley & Sons. A distance value d is measured accurately by using a conventional laser interferometry technique. In this publication the acoustic velocity in blood is stated as typically in the range from about 1540 to 1600 m/sec, in brain tissue 1510 to 1550 m/sec and in cerebrospinal fluid 1500 to 1520 m/sec.

FIG. 20 includes the various dividers, multipliers and subtracting devices or steps needed to carry out the expressions (1) and (2) above. Such methods and devices are well known in the art and need not be further explained. The values for the pulsatility of the diameter of the basal artery and cerebrospinal fluid are indicated at 210 on a display or recorder or the like.

Figure 17:
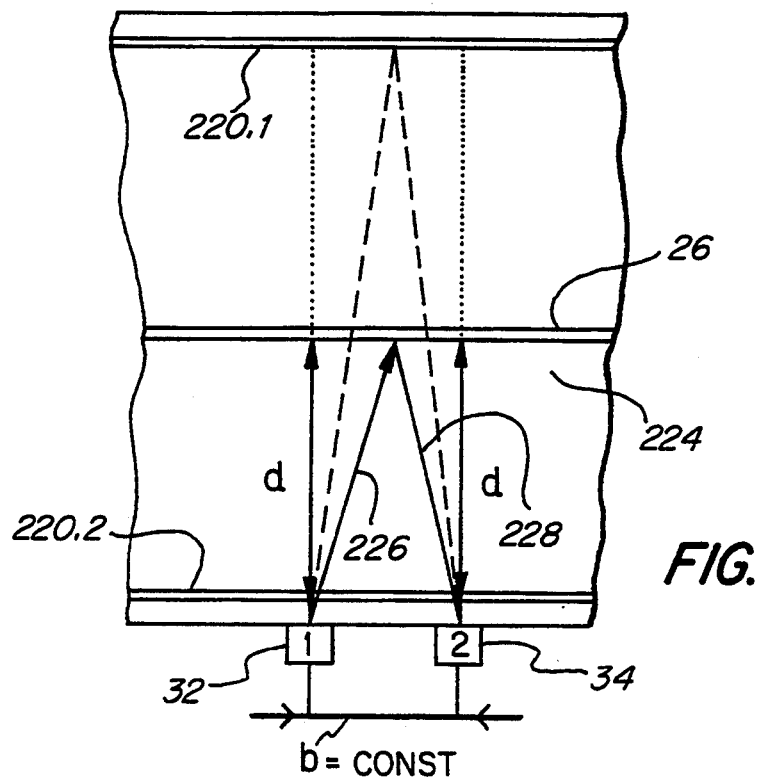
FIG. 17 is a schematic view of an alternate arrangement of ultrasonic transducers used to investigate an intracranium medium in accordance with the invention.

With reference to FIG. 17, a different arrangement of transducers 32,34 is provided to determine the velocity of acoustic pulses. In this configuration, the transducers are spaced a precise distance b from each other and detect echoes reflected by discontinuities in the intracranium medium 22 such as presented by internal surfaces 220.1 and 220.2 of the skull 56 and a surface 224 of the third ventricle 26 or a basal artery embedded in brain tissue.

If desired, the technique 200 shown in FIG. 17 can be used to derive only a signal representative of the cross-sectional dimension of the basal artery as measured along the acoustic path which intersects it.

The transducers 32,34 are operated in sequence starting for example with the injection of an acoustic pulse from the first transducer 32 and detecting echoes caused by ventricle surface 224 with both transducers. Hence, the echo detected by transducer 32 identifies a two-way travel time $\tau$ that, after division by two is directly proportional to the distance d and thus $\tau = 2d/C_t$ where $C_t$ is the acoustic velocity for brain tissue.

The echo detected by the second transducer 34 from an actuation of the first transducer 32 would follow a path as indicated by legs 226,228. The travel time $\tau$ 12 detected with transducer 34, would be defined by the following relationship:

$$\tau_{12}(t) = \frac{2\sqrt{d^2 + (0.5b)^2}}{C_t} \quad (3)$$

where b is the lateral spacing between transducers 32, 34, as shown in FIG. 17. The acoustic velocity $C_t$ in brain tissue can then be determined with the following expression:

$$C_t = b\sqrt{\frac{1}{\tau_{12}^2(t) - \tau_{22}^2(t)}} \quad (4)$$

Path induced errors in the derivation of $C_t$ can be reduced by repeating the above procedure with an activation by transducer 34 followed by echo detections by transducers 32, 34 to determine travel times $\tau_{11}$ and $\tau_{21}$ and substituting their values respectively for $\tau_{22}$ and $\tau_{12}$ in expression (4).

The different values for $C_t$ can then be combined and averaged to derive a reliable value for the acoustic velocity in brain tissue.

Figure 18:
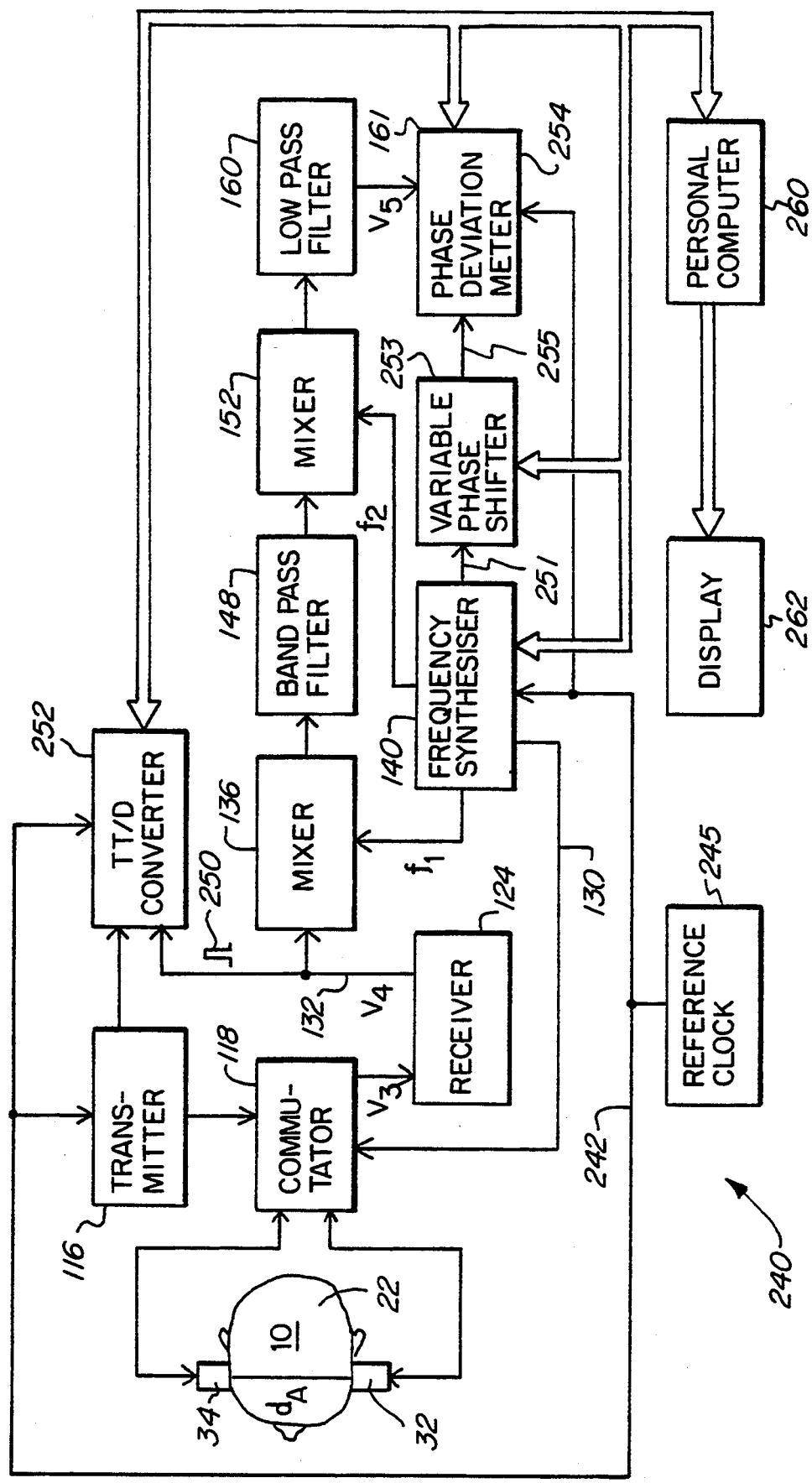
FIG. 18 is an alternate apparatus for ultrasonically investigating an intracranium medium using a phase detection technique.
Figure 19:
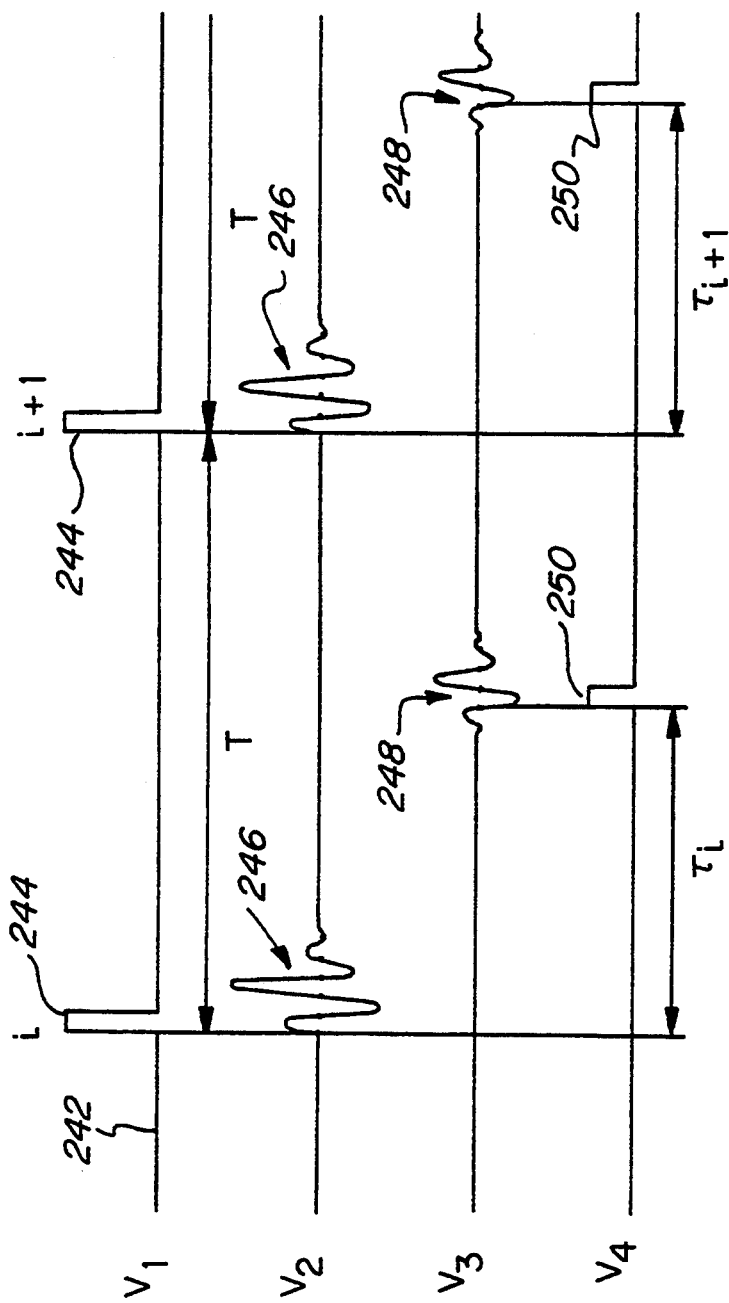
FIG. 19 is timing diagram of various signals generated in the apparatus of FIG. 18.

With reference to FIGS. 18 and 19, an alternate phase technique 240 is shown for deriving signals representative of the pulsatility of a basal artery or a ventricle and the time dependency of the pressure in brain tissue. Technique 240 employs similar devices and steps as explained with reference to FIGS. 1 and 13b and are, therefore, identified with like numerals. The output 130 of frequency synthesizer 140 in FIG. 18 is used in the same way as the output 130 of pulse generator 112 in FIG. 13a.

For purposes of illustration, a single set of transducers 32,34 is shown, used and aligned along a path A corresponding to the brain tissue path 38 illustrated in FIG. 3. The principal difference between the technique 240 in FIG. 18 and that shown in FIG. 13b is best illustrated with reference to FIGS. 19 as well as 18.

At line 242 regular clock pulses 244 separated by stable intervals T are produced from a highly stable high speed clock source 245. Each clock pulse activates transmitter 116 and causes the energization of an acoustic pulse 246 from one of the transducers 32 or 34 depending upon the status of commutator reversing switch 118. The acoustic pulses 248 incident on the receiving transducer are detected with a crossover detector/receiver 124. At the first crossover this produces output pulses 250, see FIG. 19, on a line 132. The elapsed time between the start of a clock pulse 244 and the detected receiver pulse 250 represents the acoustic interval travel, or transit, time $\tau$.

This travel time is converted to a digital format in a network 252. This typically involves the enablement of a high speed counter by a clock pulse 244 to allow the counting of high frequency clock pulses until a pulse 250 is generated by the receiver 124.

The detected pulses 250 on line 132 and thus the intervals between them, however, are applied and processed in a similar manner as described with reference to FIG. 13a through an up-mixer 136, bandpass filter 148, down-mixer 152, and a low pass filter 160.

The frequency synthesizer 140 generates the carrier frequencies $f_1$ (about 8 MHz) and $f_2$ (about 8.9995 MHz) from the clock pulses on line 242 from reference clock source 246 so that these frequencies $f_1$ and $f_2$ are synchronized to a multiple of the basic clock with an appropriate filtering circuit and is applied on an output line 251 to a phase regulator 253.

The technique 240 relies upon a phase detection to extract the time dependencies in the detected acoustic pulses 250. The technique relies upon measuring the variation in the delay time $\tau$ encountered by ultrasonic pulses passing through the intracranial medium. The delay can be expressed as $\tau_1 = \tau_0 + \Delta\tau_1$, where $$\tau_0 = \frac{d^{(A,B,C)}}{C_0^{(A,B,C)}}$$

and A,B,C, refer to the respective intracranium paths 38, 40, 42 shown in FIG. 3.

The n-th harmonic can be expressed as:

$$V_4^{(n)}(t) = V_4^{(n)} \sin n \frac{2\pi}{T} [t - (\tau_0 + \Delta_\tau(t))] \quad (5)$$

where n can be equal to the 100th harmonic; $V_4^{(n)}$ is the amplitude of the nth harmonic; $\tau_0$ is the constant part of the delay time; and $\Delta_\tau(t)$ is the modulated part and the desired parameter signal; and $\tau_0 + \Delta_\tau^{(1)}(t_1) = \tau_i$.

After mixing $V_4^{(n)}(t)$ in mixer 136, filtering by bandpass filter 148, mixing in mixer 152 and filtering by lowpass filter 160 the following sinusoidal signal $V_5$ appears on the output 161 of filter 160:

$$V_5(t) = V_5 \sin\left[\left(n\frac{1}{T} + f_1 - f_2\right)2\pi(t - \tau_0) + n\frac{2\pi}{T}\Delta_\tau(t)\right] \quad (6)$$

A phase deviation meter 254 is used to determine the time variable part of the phase attributable to changes in the path d. Phase deviation meter 254 compares an adjusted phase output from the variable phase shifter 253 on line 255 with the phase of the signal on line 161. Since $$n\frac{1}{T} + f_1 - f_2 = F$$

is a constant, the expression (6) can be simplified in the case where $F = 1/\tau$ to:

$$V_5(t) = V_5 \sin\left[\frac{2\pi}{T}(t - \tau_0) + \frac{2\pi}{T}n\Delta_\tau(t)\right] \quad (7)$$

which is substantially the same as the first harmonic of $V_4$, the signal on line 132 because the total time delay $\tau_S$ introduced by the effect of the mixers 136, 160 and band pass filter 148 is much less than $\tau_0$.

In order to derive a parameter signal, namely the variation in the positions of the pulses 250 due to changes in the intracranium medium, it is necessary to adjust the phase of the frequency synthesizer 140 output 251 signal by a value that is equivalent to the delay measured with the converter 252. Its measured value is, therefore, applied under control by a computer 260 to the variable phase shifter 253 which produces an output signal on line 255 representative of the desired phase shift:

$$\Phi_0 = \frac{2\Pi}{T} \tau_0.$$

The output from phase divation meter 254 is a parameter signal that is in digitized form with the use of high speed clock pulses on line 242 and displayed at 262 under control by computer 260.

Figure 23:
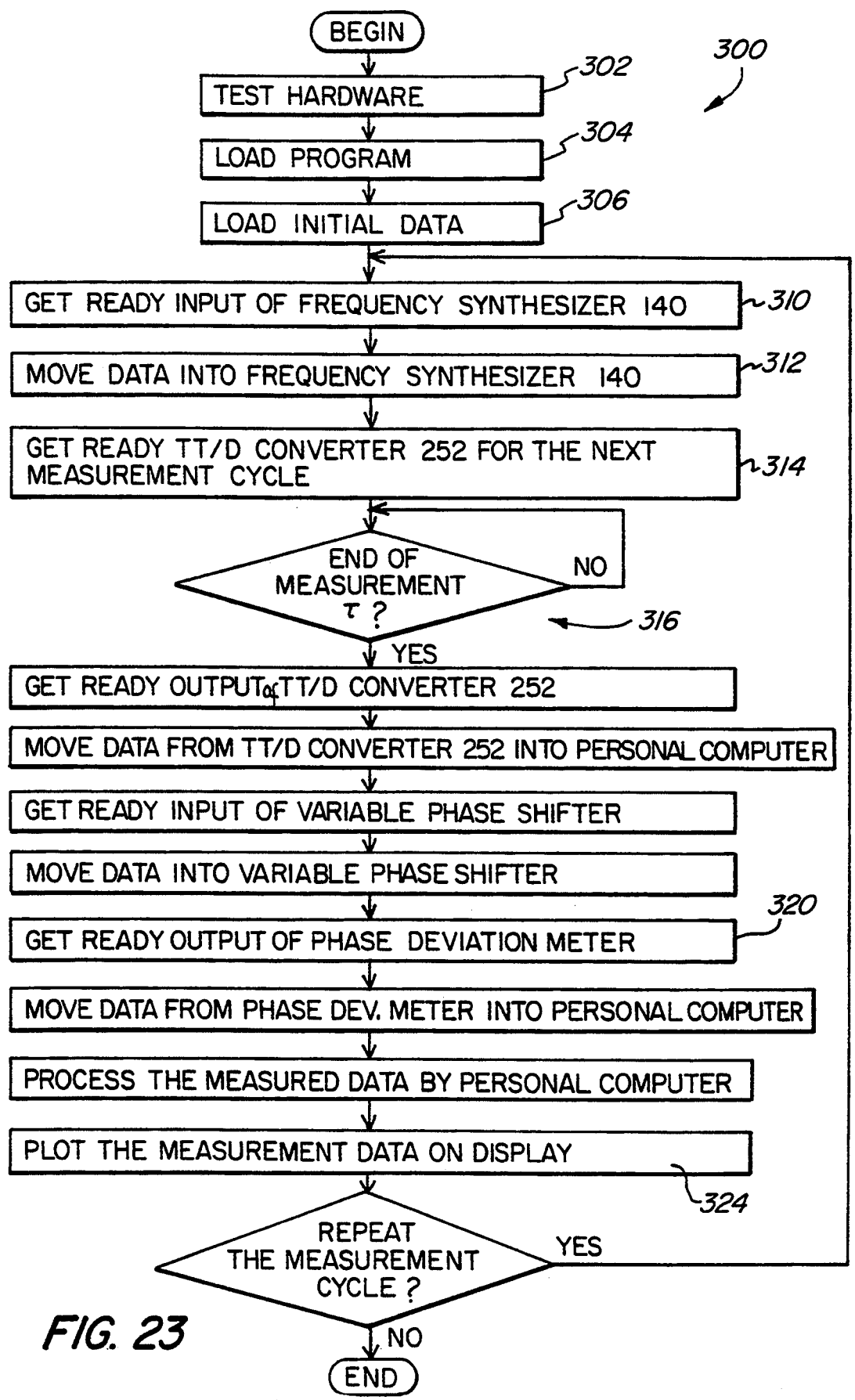
FIG. 23 is a flow chart for program steps for the computer shown in FIG. 18.

With reference to FIG. 23, a technique 300 is shown for operating a computer controlled system for an embodiment as illustrated in FIG. 18. The test hardware programs and appropriate initial data are set up at steps 302, 304 and 306.

An acoustic measurement is begun by initializing the frequency synthesizer 140 at 310 and 312 and the travel time converter at 314.

Acoustic measurements are then made at 316 to derive the parameter signal from the phasemeter at 320 and plot the result at 324.

Having thus described several embodiments of the invention, its advantages can be understood. Variations can be made without departing from the scope of the claims set forth herein. For example, much of the apparatus and techniques described herein can be performed with a digital computer programmed to perform the frequency conversions and frequency measurements as well as the other functions described. Digitizing of signals may utilize appropriate analog-to-digital converters.

What is claimed is:

1. A method of deriving an indication of a characteristic of an intracranial medium in a non-invasive manner, comprising the steps of:
    deriving repetitive transit time signals representative of the travel times of ultrasonic pulses generated at a first frequency along an acoustic path within the intraeranial medium as well as variations in the travel times attributable to physical changes of a portion of the intracranial medium along the acoustic path;
    extracting from said transit time signals at a substantially higher frequency spectrum than the first frequency, signal portions representative of said physical changes; and
    indicating said signal portions as representative of a characteristic of the intracranial medium.

2. The method of deriving an indication of a characteristic of the intracranial medium as claimed in claim 1 wherein said acoustic path intersects a basal artery; and
    wherein said extracting step comprises the step of extracting signal portions representative of pulsatility of the diameter of the basal artery intersected by said acoustic path.

3. The method of deriving an indication of a characteristic of the intracranial medium as claimed in claim 1 wherein said acoustic path intersects a cerebral ventricle; and
    wherein said extracting step comprises the step of extracting signal portions representative of pulsatility of the cerebral ventricle intersected by said acoustic path.

4. The method of deriving an indication of a characteristic of the intracranial medium as claimed in claim 1;
    wherein said extracting step comprises the step of extracting signals portions representative of variations of the intracranial pressure along said acoustic path.

5. The method of deriving an indication of a characteristic of the intracranial medium as claimed in claim 4 wherein said acoustic path intersects a basal artery;
    and wherein said extracting step further includes the step of extracting signal portions representative of pulsatility of the basal artery; and
    combining signal portions representative of the pulsatility of the basal artery with said signals representative of the brain tissue in accordance with a predetermined relationship so as to produce a parameter signal representative of a cross-sectional dimension of the basal artery along the acoustic path which intersects the basal artery.

6. The method of deriving an indication of a characteristic of the intracranial medium as claimed in claim 4 wherein said acoustic path intersects a cerebral ventricle;
    and wherein said extracting step further includes the step of extracting signal portions representative of pulsatility of the cerebral ventricle; and
    combining signal portions representative of the pulsatility of the cerebral ventricle with said signals representative of the brain tissue in accordance with a predetermined relationship so as to produce a parameter signal representative of a cross-sectional dimension of the cerebral ventricle along the acoustic path which intersects the cerebral ventricle.

7. The method of deriving an indication of a characteristic of the intracranial medium as claimed in claim 1 wherein the step of deriving transit time signals derives transit time signals representative of different acoustic paths which intersect respectively a basal artery, a cerebral ventricle and primarily brain tissue;
    and wherein said extracting step comprises the step of extracting different signal portions respectively representative of time dependent characteristics of the basal artery, the cerebral ventricle and the brain tissue.

8. The method of deriving an indication of a characteristic of the intracranial medium as claimed in claim 7 and further including the step of
    combining extracted signal portions in accordance with predetermined relationships to derive parameter signals respectively representative of dimensions of said basal artery and of said cerebral ventricle along respective acoustic paths.

9. A method of deriving an indication of a characteristic of an intracranial medium in a non-invasive manner, comprising the steps of:
    deriving transit time signals representative of the travel times of ultrasonic pulses along an acoustic path within the intracranial medium as well as variations in the travel times attributable to physical changes of a portion of the intracranial medium along the acoustic path;

extracting from said transit time signals, signal portions representative of said changes;

indicating said signal portions as representative of a characteristic of the intracranial medium;

wherein said deriving step comprises deriving a train of transit time signals at a repetition frequency which has a variable component primarily attributable to cardiac induced changes of a portion of the physical medium along said acoustic investigation path, said transit time signals having higher harmonics which are spaced at frequency intervals determined by whole integer multiples of said repetition frequency;

increasing the frequency domain of the transit time signals;

selecting, from the increased frequency domain, a frequency band which contains a first whole integer multiple harmonic of the variable component of said repetition frequency;

deriving from the selected frequency band a first whole integer multiple of the variable component as a first parameter signal representative of the physical changes of the intracranium medium along said acoustic investigation path.

10. The method of deriving an indication of a characteristic of the intracranial medium as claimed in claim 9 wherein said step of deriving the first parameter signal comprises the steps of:

down-shifting the frequency of the selected frequency band; and extracting said first parameter signal from the down-shifted frequency band.

11. A method of deriving an indication of a characteristic of an intracranial medium in a non-invasive manner, comprising the steps of:

placing ultrasonic transducers on a skull with an alignment selected so that an acoustic investigation path intersects a desired region within the intracranial medium;

activating said transducers so as to deliver acoustic pulses at a desired pulse rate along said acoustic investigation path;

generating transit time signals representative of the travel times of ultrasonic pulses along the acoustic path within the intracranial medium as well as variations in the travel times attributable to physical changes of a portion of the intracranial medium along the acoustic path;

generating a substantially higher frequency spectrum of the transit time signals than the desired pulse rate of the acoustic pulses;

extracting from said transit time signals at said substantially higher frequency spectrum, signal portions representative of said changes; and indicating said signal portions as representative of a characteristic of the intracranial medium.

12. The method of deriving an indication of a characteristic of the intracranial medium as claimed in claim 11 wherein said placing step places ultrasonic transducers on a skull with an alignment selected so that said acoustic path intersects a basal artery; and wherein said extracting step comprises the step of extracting signal portions representative of pulsatility of the diameter of the basal artery intersected by said acoustic path.

13. The method of deriving an indication of a characteristic of the intracranial medium as claimed in claim 11 wherein said placing step places ultrasonic transducers on a skull with an alignment selected so that said acoustic path intersects a cerebral ventricle; and wherein said extracting step comprises the step of extracting signal portions representative of pulsatility of the cerebral ventricle intersected by said acoustic path.

14. The method of deriving an indication of a characteristic of the intracranial medium as claimed in claim 11 wherein said placing step places ultrasonic transducers on a skull with an alignment selected so that said acoustic path intersects the intracranial medium;

and wherein said extracting step comprises the step of extracting signals portions representative of time dependencies in the intracranium pressure of the brain tissue intersected by said acoustic path.

15. The method of deriving an indication of a characteristic of the intracranial medium as claimed in claim 14 wherein the placing step places ultrasonic transducers on a skull with an alignment selected so that an acoustic path intersects a basal artery;

and wherein said extracting step further includes the step of extracting signal portions representative of pulsatility of the basal artery; and combining signal portions representative of the pulsatility of the basal artery with said signals representative of the brain tissue in accordance with a predetermined relationship so as to produce a parameter signal representative of a cross-sectional dimension of the basal artery along the acoustic path which intersects the basal artery.

16. The method of deriving an indication of a characteristic of the intracranial medium as claimed in claim 14 wherein the placing step places ultrasonic transducers on a skull with an alignment selected so that an acoustic path intersects a cerebral ventricle;

and wherein said extracting step further includes the step of extracting signal portions representative of pulsatility of the cerebral ventricle; and combining signal portions representative of the pulsatility of the cerebral ventricle with said signals representative of the brain tissue in accordance with a predetermined relationship so as to produce a parameter signal representative of a cross-sectional dimension of the cerebral ventricle along the acoustic path which intersects the cerebral ventricle.

17. The method of deriving an indication of a characteristic of the intracranial medium as claimed in claim 11 wherein the placing step places ultrasonic transducers on a skull in respectively different alignments so as to cause ultrasonic pulses to travel along different acoustic paths selected to intersect respectively a basal artery, a cerebral ventricle and primarily brain tissue;

and wherein said extracting step comprises the step of extracting different signal portions respectively representative of time dependent characteristics of the basal artery, the cerebral ventricle and the brain tissue.

18. The method of deriving an indication of a characteristic of the intracranial medium as claimed in claim 17 and further including the step of combining extracted signal portions in accordance with predetermined relationships to derive parameter signals respectively representative of cross-sectional dimensions of said basal artery and of said cerebral ventricle along respective acoustic paths.

19. The method as claimed in claim 11 wherein the step of placing said transducers comprises placing the transducers in a fixed spatial relationship on opposite sides of the skull so that the acoustic investigating path between the transducers passes through the desired region of the intracranium medium.

20. The method as claimed in claim 11 wherein the placing step comprises placing the transducers on the same side of the skull in a fixed spatial relationship so as to form an acoustic investigation path which is incident upon and reflects from an acoustic discontinuity within the intracranium medium.

21. A method for deriving an indication of a characteristic of a living physical medium in a non-invasive manner, comprising the steps of:
deriving a train of transit time signals at a repetition frequency which has a variable component primarily attributable to cardiac induced physical changes of a portion of the physical medium along an acoustic investigation path, said transit time signals having a range of higher harmonics which are spaced in the frequency domain at intervals determined by whole integer multiples of said repetition frequency;
up-shifting the frequency domain of the transit time signals with their higher harmonics;
selecting, from the up-shifted frequency domain a frequency band containing a first whole integer multiple harmonic whose frequency is sufficiently high so as to be effectively above the noise spectrum in the train of said transit time signals;
down-shifting the frequency domain of the selected frequency band;
extracting, from the down-shifted frequency domain, a first whole integer multiple of the variable component of said repetition frequency as a first parameter signal representative of the physical changes of the physical medium along said acoustic investigation path.

22. The method as claimed in claim 21 and further comprising the steps of:
selecting a second frequency band containing a second whole integer multiple harmonic whose frequency is sufficiently high so as to be effectively above the noise spectrum in the train of said transit time signals;
deriving from said second frequency band a second whole integer multiple of the variable component of said repetition frequency as a second parameter signal representative of the physical changes of the physical medium along said acoustic investigation path; and
combining the first and second parameter signals to produce an improved parameter signal representative of the changes of the physical medium along the acoustic investigation path.

23. An apparatus for deriving an indication of a characteristic of an intracranial medium in a non-invasive manner comprising:
means for generating transit time signals representative of the travel times of ultrasonic pulses injected into the intracranial medium at a desired pulse rate along a desired acoustic investigation path within the intracranial medium as well as representative of variations of said travel times attributable to cardiac induced changes of at least a portion of the intracranial medium along said acoustic path;
means for extracting signal portions from a frequency spectrum of said transit time signals and which are substantially higher in frequency than said desired pulse rate, and wherein said signal portions are representative of said variations to form a first parameter signal representative of said changes; and
means for indicating said first parameter signal.

24. An apparatus for deriving an indication of a characteristic of an intracranial medium in a non-invasive manner comprising:
means for generating transit time signals representative of the travel times of ultrasonic pulses along a desired acoustic investigation path within the intracranial medium as well as variations of said travel times attributable to cardiac induced changes of at least a portion of the intracranial medium along said acoustic path;
means for extracting signal portions from said transit time signals representative of said variations to form a first parameter signal representative of said changes;
means for indicating said first parameter signal;
wherein said transit time signals generating means comprises:
means for producing a train of transit time signals at a repetition frequency which has a variable component primarily attributable to cardiac induced changes of a portion of the physical medium along said acoustic investigation path, said transit time signals having higher harmonics which are spaced at frequency intervals determined by whole integer multiples of said repetition frequency;
means for increasing the frequency domain of the transit time signals; and
wherein said means for extracting signal portions further includes:
means for selecting, from the increased frequency domain, a frequency band which contains a first whole integer multiple harmonic of the variable component of said repetition frequency; and means for deriving from the selected frequency band a first whole integer multiple of the variable component as said first parameter signal representative of the changes of the intracranium medium along said acoustic investigation path.

25. The apparatus as claimed in claim 24 wherein said means for deriving the first parameter signal further comprises:
means for down-shifting the frequency of the selected frequency band; and
means for extracting said first parameter signal from the down-shifted frequency band.

26. The apparatus as claimed in claim 25 wherein said means for increasing the frequency domain comprises:
means for generating a first carrier signal; and
first mixer means coupled to said transit time signals and the first carrier signal for amplitude modulating said first carrier signal with said transit time signals;
wherein said means for downshifting the frequency of the selected passband includes:
means for generating a second carrier signal;
second mixer means coupled to said selected frequency band and said second carrier signals for amplitude modulating said selected frequency band with said second carrier signal; and
wherein said means for extracting said first parameter signal includes a low pass filter effectively coupled to an output of said second mixer means.

27. An apparatus for deriving an indication of a characteristic of an intracranial medium in a non-invasive manner comprising:

means for generating transit time signals representative of the travel times of ultrasonic pulses along a desired acoustic investigation path within the intracranial medium as well as variations of said travel times attributable to cardiac induced changes of at least a portion of the intracranial medium along said acoustic path;

means for extracting signal portions from said transit time signals representative of said variations to form a first parameter signal representative of said changes;

means for indicating said first parameter signal;

wherein the extracting means comprises:

first channel means for extracting said signal portions from a first harmonic whose frequency is effectively above the frequency spectrum of noise in said transit time signals and produce said first parameter signal;

second channel means for extracting signal portions from a second harmonic whose frequency is effectively above the frequency spectrum of noise in said transit time signals and produce a second parameter signal indicative of variations of said travel times attributable to cardiac-induced changes of at least said portion of the intracranium medium; and means for combining said first and second parameter signals to produce a third parameter signal with improved accuracy.

28. The apparatus as claimed in claim 27 wherein said combining means includes means for generating an average of said first and second parameter signals as said third parameter signal.

29. An apparatus for producing an indication of a characteristic of a living physical medium in a non-invasive manner, comprising:

means for deriving a train of transit time signals at a repetition frequency which has a variable component primarily attributable to cardiac induced physical changes of a portion of the physical medium along an acoustic investigation path, said transit time signals having a range of higher harmonics which are spaced in the frequency domain at intervals determined by whole integer multiples of said repetition frequency;

means for up-shifting the frequency domain of the transit time signals with their higher harmonics;

means for selecting, from the up-shifted frequency domain a frequency band containing a first whole integer multiple harmonic whose frequency is sufficiently high so as to be effectively above the noise spectrum in the train of said transit time signals;

means for down-shifting the frequency domain of the selected frequency band;

means for extracting, from the down-shifted frequency domain, a first whole integer multiple of the variable component of said repetition frequency as a first parameter signal representative of the physical changes of the physical medium along said acoustic investigation path.

30. The apparatus as claimed in claim 29 and further comprising:

means for selecting a second frequency band containing a second whole integer multiple harmonic whose frequency is sufficiently high so as to be effectively above the noise spectrum in the train of said transit time signals;

means for deriving from said second frequency band a second whole integer multiple of the variable component of said repetition frequency as a second parameter signal representative of the physical changes of the physical medium along said acoustic investigation path; and means for combining the first and second parameter signals to produce an improved parameter signal representative of the changes of the physical medium along the acoustic investigation path.

* * * * *